US010435381B2

(12) United States Patent
Teles et al.

(10) Patent No.: US 10,435,381 B2
(45) Date of Patent: Oct. 8, 2019

(54) PROCESS FOR PREPARING PROPYLENE OXIDE

(71) Applicants: BASF SE, Ludwigshafen am Rhein (DE); Dow Global Technologies LLC, Midland, MI (US)

(72) Inventors: Joaquim Henrique Teles, Ludwigshafen am Rhein (DE); Marvin Kramp, Ludwigshafen am Rhein (DE); Christian Mueller, Ludwigshafen am Rhein (DE); Nicolai Tonio Woerz, Ludwigshafen am Rhein (DE); Bernd Metzen, Ludwigshafen am Rhein (DE); Tobias Keller, Ludwigshafen am Rhein (DE); Dominic Riedel, Ludwigshafen am Rhein (DE); Heiner Schelling, Ludwigshafen am Rhein (DE); Markus Weber, Ludwigshafen am Rhein (DE); Daniel Urbanczyk, Ludwigshafen am Rhein (DE); Andrei-Nicolae Parvulescu, Ludwigshafen am Rhein (DE); Ulrike Wegerle, Worms (DE); Ulrich Mueller, Ludwigshafen am Rhein (DE); Meinolf Weidenbach, Stade (DE); Werner J. Witzl, Stade (DE); Karsten Luecke, Stade (DE)

(73) Assignees: BASF SE, Ludwigshafen am Rhein (DE); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/318,221

(22) PCT Filed: Jul. 19, 2017

(86) PCT No.: PCT/EP2017/068223
§ 371 (c)(1),
(2) Date: Jan. 16, 2019

(87) PCT Pub. No.: WO2018/015430
PCT Pub. Date: Jan. 25, 2018

(65) Prior Publication Data
US 2019/0169149 A1 Jun. 6, 2019

(30) Foreign Application Priority Data
Jul. 20, 2016 (EP) ..................... 16180293

(51) Int. Cl.
| C07D 301/32 | (2006.01) |
| C07D 301/12 | (2006.01) |
| C07D 303/04 | (2006.01) |
| B01D 3/00 | (2006.01) |
| B01D 3/14 | (2006.01) |
| B01D 5/00 | (2006.01) |

(Continued)

(52) U.S. Cl.
CPC ........... *C07D 301/32* (2013.01); *B01D 3/009* (2013.01); *B01D 3/143* (2013.01); *B01D 3/40* (2013.01); *B01D 5/006* (2013.01); *C07D 301/12* (2013.01); *B01J 29/085* (2013.01); *C07D 303/04* (2013.01)

(58) Field of Classification Search
CPC .. C07D 301/32; C07D 301/12; C07D 303/04; B01D 3/008; B01D 3/143; B01D 3/40; B01D 5/006; B01J 29/085
See application file for complete search history.

(56) References Cited

U.S. PATENT DOCUMENTS

| 2003/0162983 A1 | 8/2003 | Strebelle et al. |
| 2004/0142933 A1 | 7/2004 | Forrest et al. |

(Continued)

FOREIGN PATENT DOCUMENTS

| EP | 1 122 249 A1 | 8/2001 |
| WO | WO 2004/037802 A1 | 5/2004 |

(Continued)

OTHER PUBLICATIONS

Ullmann's Encyclopedia of Industrial Chemistry, $5^{th}$ Edition, vol. A13, 1989, pp. 443-466.

(Continued)

*Primary Examiner* — Timothy R Rozof
(74) *Attorney, Agent, or Firm* — Oblon, McClelland, Maier & Neustadt, L.L.P.

(57) ABSTRACT

The present invention is related to a process for preparing propylene oxide, comprising (i) providing a stream comprising propene, hydrogen peroxide or a source of hydrogen peroxide, water, and an organic solvent; (ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propylene oxide, water, and the organic solvent; (iii) removing an effluent stream from the epoxidation zone, the effluent stream comprising propylene oxide, water, organic solvent, and propene; (iv) separating propene from the effluent stream by distillation, comprising (iv.1) subjecting the effluent stream to distillation conditions in a distillation unit, obtaining a gaseous top stream S0 enriched in propene compared to the effluent stream subjected to distillation conditions, and a liquid bottoms stream S01 enriched in propylene oxide, water and organic solvent compared to the effluent stream subjected to distillation conditions; (iv.2) returning a condensed portion of the stream S0 to an upper part of the distillation unit.

15 Claims, 3 Drawing Sheets

Figure 1:
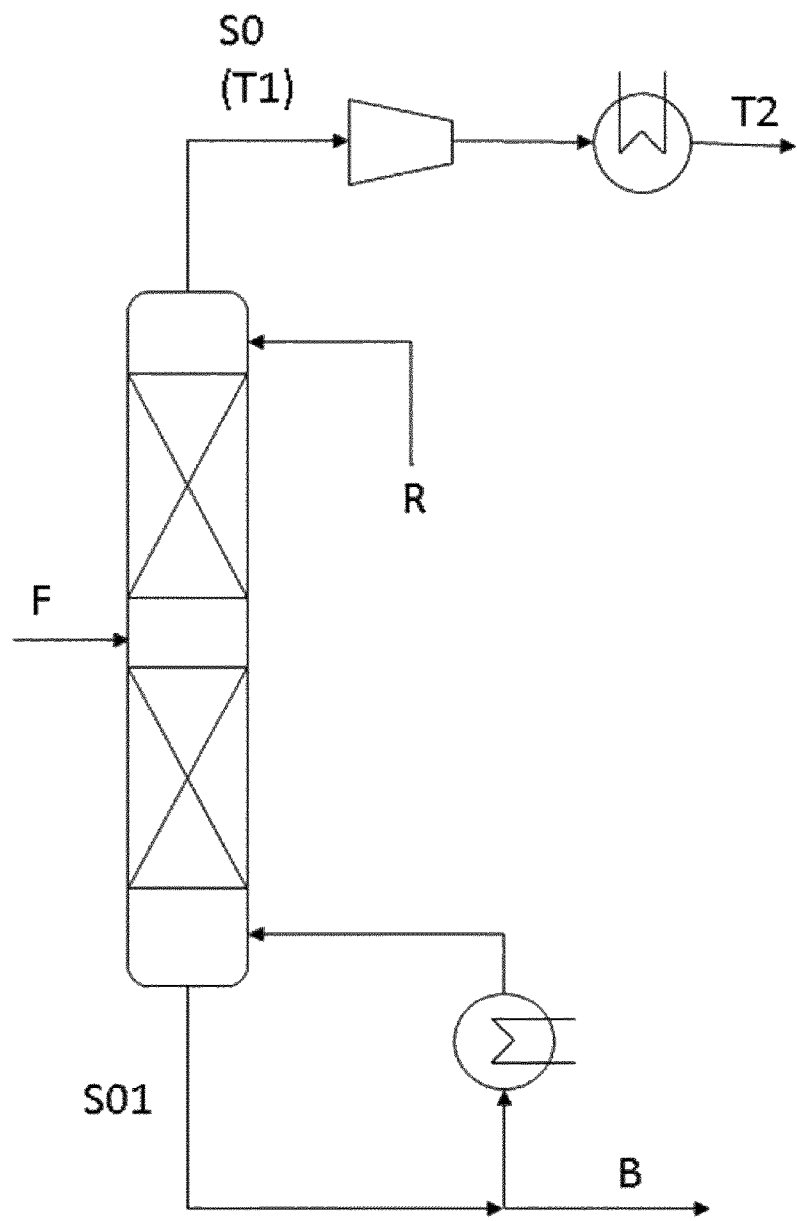

(51) Int. Cl.
*B01D 3/40* (2006.01)
*B01J 29/08* (2006.01)

(56) References Cited

U.S. PATENT DOCUMENTS

2006/0058539 A1 3/2006 Babler et al.
2008/0230369 A1 9/2008 Chang
2016/0176835 A1 6/2016 Riedel et al.

FOREIGN PATENT DOCUMENTS

| WO | WO 2008/118265 A1 | 10/2008 |
| WO | WO 2009/008493 A2 | 1/2009 |
| WO | WO 2015/010990 A1 | 1/2015 |
| WO | WO 2015/049327 A1 | 4/2015 |

OTHER PUBLICATIONS

International Preliminary Report on Patentability and Written Opinion dated Jan. 31, 2019 in PCT/EP2017/068223, 7 pages.

PROCESS FOR PREPARING PROPYLENE OXIDE

The present invention is directed to a process for preparing propylene oxide, wherein propene is separated by distillation from an effluent stream from an epoxidation zone, said effluent stream comprising propylene oxide, water, organic solvent, and propene, wherein the effluent stream is subjected to distillation conditions in a distillation unit and a condensed portion of a gaseous top stream, which is enriched in propene, is returned to an upper part of the distillation unit.

Propylene oxide is an important intermediate in the chemical industry. A suitable process for the preparation of propylene oxide starts from propene and makes use of hydrogen peroxide as oxidizing agent, of a solvent and of an epoxidation catalyst comprising a titanium zeolite. Due to its importance for industrial-scale processes, it is desired to carry out the epoxidation reaction as efficiently as possible and to purify the propylene oxide to a high degree. The epoxidation reaction results in a mixture comprising solvent, water and propylene oxide. Since the epoxidation is usually carried out with an excess on propene the resulting mixture comprises also varying amounts of propene. Especially in industrial-scale continuous processes for the epoxidation of propene in a solvent, one feature of the overall process is the recycling of the propene back into the epoxidation step. Since propylene oxide is volatile, the separation of non-reacted propene is challenging if the entrainment of propylene oxide is to be avoided. An entrainment of propylene oxide would require further work-up steps, because a return of propylene oxide to the epoxidation reactor would result in the enhanced formation of undesired side products.

WO 2008/118265 A discloses an extractive distillation with methanol and/or water in order to separate propene from propylene oxide. The mixture to be separated results from an epoxidation of propene with hydrogen peroxide or $H_2/O_2$-mixtures and comprises methanol as solvent. Thus, mixtures of methanol and water are the preferred solvents for the extraction distillation, which come from a follow-up stage of the process. The method has the disadvantage that an additional inner loop is established in the process, which results in larger streams and also in the risk that side products accumulate in the loop. Especially the increase in hydraulic load results in a higher energy consumption. WO 2004/037802 A discloses a similar method based on a process, where propylene oxide is prepared from propene and hydrogen peroxide in acetonitrile. The disadvantages are comparable to those described above with respect to WO 2008/118265 A.

Although the boiling points of propylene oxide and propene differ from each other, the separation of both compounds is challenging. Their separation in a conventional distillation, where the top condenser runs with cooling water, the condensation temperature at the top would have to be above 40° C., thus requiring a top pressure of at least 16.5 bar. However, a pressure of 16.5 bar would result in a sump temperature of at least 140° C., which would result in thermal decomposition of propylene oxide. Even if one would use cold water (temperature 5° C.) for running the top condenser, this would also result in a top pressure of at least 6.5 bar. This pressure would result in a sump temperature of at least 100° C., where propylene oxide also thermally decomposes to a substantial extent.

It was therefore an object of the present invention to provide a process for the separation of propylene oxide and propene which is efficient and allows to essentially avoid both the decomposition of the propylene oxide in the sump and losses of propylene oxide overhead. The process should be economically advantageous and should especially allow to reduce the energy consumption of the separation of propylene oxide and propene.

Surprisingly, it was found that if in the destillative separation of propene from an effluent stream, said effluent stream comprising propylene oxide, water, organic solvent, propene, and propane; a condensed portion of a gaseous top stream S0, which is enriched in propene, is returned to an upper part of the distillation unit, the separation of propene from propylene oxide can be positively influenced, while a decomposition of the propylene oxide can be avoided and the energy consumption can be lowered.

Therefore, the present invention relates to a process for preparing propylene oxide, comprising
(i) providing a stream comprising propene, hydrogen peroxide or a source of hydrogen peroxide, water, and an organic solvent;
(ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propylene oxide, water, and the organic solvent;
(iii) removing an effluent stream from the epoxidation zone, the effluent stream comprising propylene oxide, water, organic solvent, and propene;
(iv) separating propene from the effluent stream by distillation, comprising
(iv.1) subjecting the effluent stream to distillation conditions in a distillation unit, obtaining a gaseous top stream S0 enriched in propene compared to the effluent stream subjected to distillation conditions, and a liquid bottoms stream S01 enriched in propylene oxide, water and organic solvent compared to the effluent stream subjected to distillation conditions;
(iv.2) returning a condensed portion of the stream S0 to an upper part of the distillation unit.

Preferably, the process is a continuous process.

Generally, it is conceivable to use a pure or essentially pure propene as starting material and as part of the stream subjected to the epoxidation in (ii). Preferably, a mixture of propene and propene is used. Most preferably a technical propylene grade according to an international norm like for instance ASTM D5273 or DIN 51622 is used.

Therefore, the present invention also relates to a process for preparing propylene oxide, comprising
(i) providing a stream comprising propene, propane, hydrogen peroxide or a source of hydrogen peroxide, water, and an organic solvent;
(ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and the organic solvent;
(iii) removing an effluent stream from the epoxidation zone, the effluent stream comprising propylene oxide, water, organic solvent, propene, and propane;
(iv) separating propene and propane from the effluent stream by distillation, comprising
(iv.1) subjecting the effluent stream to distillation conditions in a distillation unit, obtaining a gaseous top stream S0 enriched in propene and propane compared to the effluent stream subjected to distillation conditions, and a liquid bottoms stream S01 enriched in propylene oxide, water and organic solvent compared to the effluent stream subjected to distillation conditions;

(iv.2) returning a condensed portion of the stream S0 to an upper part of the distillation unit.

If a mixture of propene and propane is used as part of the stream provided in (i) and subjected to the epoxidation in (ii), the weight ratio of propene:propane is preferably at least 7:3. For example, commercially available propene can be employed which may be either a polymer grade propene or a chemical grade propene. Typically, polymer grade propene has a propene content in the range of from 99 to 99.8 weight-% and a propane content in the range of from 0.2 to 1 weight-%. Chemical grade propene typically has a propene content in the range of from 92 to 98 weight-% and a propane content in the range of from 2 to 8 weight-%. According to a preferred embodiment of the present invention, a mixture of propene and propane is subjected to the epoxidation which has a propene content in the range of from 99 to 99.8 weight-% and a propane content in the range of from 0.2 to 1 weight-%.

Effluent Stream

Generally, there is no specific restriction with respect to the composition of the effluent stream, provided that it comprises propylene oxide, water, organic solvent, propene, and optionally propane. Preferably, at least 95 weight-%, more preferably from 95 to 100 weight-%, more preferably from 98 to 100 weight-%, more preferably from 99 to 100 weight-%, of the effluent stream removed in (iii) consist of propylene oxide, the organic solvent, water, propene, oxygen, and optionally propane.

Preferably, the effluent stream removed in (iii) comprises the propylene oxide in amount of from 5 to 20 weight-%, more preferably from 8 to 18 weight-%, more preferably from 10 to 14 weight-%, based on the total weight of the effluent stream; the organic solvent in amount of from 60 to 75 weight-%, more preferably from 65 to 70 weight-%, based on the total weight of the effluent stream; the water in amount of from 10 to 25 weight-%, more preferably from 15 to 20 weight-%, based on the total weight of the effluent stream; the propene in amount of from 1 to 5 weight-%, more preferably from 3 to 4.5 weight-%, based on the total weight of the effluent stream; oxygen in an amount of from 0.05 to 1 weight-%, more preferably from 0.1 to 0.5 weight-%, based on the total weight of the effluent stream; and optionally the propane in amount of from 0.1 to 2 weight-%, more preferably from 0.2 to 1 weight-%, based on the total weight of the effluent stream.

Distillation Conditions

According to (iv), the effluent stream is subjected in (iv.1) to distillation conditions in a distillation unit. Generally, there is no specific restriction with respect to the design of the distillation unit, provided that is suitable for carrying out the separation of propene. Preferably, the distillation unit employed in (iv) is at least one distillation tower, more preferably one distillation tower, wherein the distillation tower has from 3 to 50, preferably from 5 to 15, more preferably from 6 to 10, more preferably from 7 to 9, theoretical trays. Preferably, the rectifying section of the distillation unit consists of from 50 to 75%, preferably of from 60 to 65%, of the theoretical trays and the stripping section of the distillation unit consists of from 25 to 50%, preferably of from 35 to 40%, of the theoretical trays. Preferably, the distillation unit employed in (iv) is operated at a top pressure of from 0.5 to 2.8 bar, preferably from 0.6 to 2.5 bar, more preferably of from 0.8 to 1.5 bar. Preferably, the distillation unit employed in (iv) is operated at a top temperature in the range of from −70 to −30° C., preferably of from −60 to −40° C., more preferably of from −55 to −45° C.

Epoxidation Zone

According to (ii), the liquid feed stream provided in (i) is subjected to epoxidation reaction conditions in an epoxidation zone, wherein a reaction mixture comprising propene, propylene oxide, water, and the organic solvent is obtained.

Generally, there are no specific restrictions regarding the design of the epoxidation zone provided that it is suitable for carrying out a, preferably continuous, epoxidation reaction. Preferably, the epoxidation zone according to (ii) comprises one or more epoxidation subzone wherein a given epoxidation subzone preferably consist of one or more epoxidation reactors wherein, with regard to the design of the one or more epoxidation reactors, no specific restrictions exist provided that the reactors are suitable for carrying out a continuous epoxidation reaction.

Preferably, the epoxidation zone according to (ii) comprises a first epoxidation subzone consisting of one or more epoxidation reactors A. The term "first epoxidation subzone" as used in this context of the present invention relates to the epoxidation subzone into which the liquid feed stream provided in (i) is passed, wherein the epoxidation zone of (ii) may comprise further epoxidation subzones which are arranged downstream of the first epoxidation subzone. If the first epoxidation subzone consisting of two or more epoxidation reactors A, it is preferred that the two or more epoxidation reactors A are arranged in parallel. In this case, it is preferred that in (ii), the liquid feed stream provided in (i) is passed into at least one of the epoxidation reactors A. It is possible, for example, that, while the liquid feed stream provided in (i) is passed into at least one of the epoxidation reactors A, at least one of the reactors A is taken out of operation, for example for maintenance purposes and/or for regenerating the catalyst comprised in the at least one of the reactors A. If the first epoxidation subzone comprises two or more epoxidation reactors A, the reactors in operation are operated essentially identically so that in every epoxidation reactor A in operation, a given epoxidation condition is in the same range in every reactor.

The epoxidation conditions according to (ii) comprise an epoxidation temperature TN, wherein TN is the temperature of a heat transfer medium used for adjusting the temperature of the reaction mixture in the first epoxidation reaction subzone according to (ii) wherein it is preferred that said temperature is adjusted by passing the heat transfer medium through a jacket of the one or more epoxidation reactors A, wherein TN is preferably the temperature of the heat transfer medium prior to adjusting the temperature of the reaction mixture, preferably the temperature of the heat transfer medium at the entrance of the jacket of the one or more epoxidation reactors A. If the first epoxidation subzone comprises two or more epoxidation reactors A, the epoxidation temperature TN relates to the epoxidation temperature TN of a given reactor A in operation of first epoxidation subzone.

Preferably, the epoxidation conditions according to (ii) comprise a first epoxidation reaction pressure in the range of from 14 to 100 bar, more preferably in the range of from 15 to 32 bar, more preferably in the range of from 15 to 25 bar. The first epoxidation reaction pressure is defined as the absolute pressure at the exit of the first epoxidation subzone. If the first epoxidation subzone comprises two or more epoxidation reactors A, the first epoxidation reaction pressure relates to the absolute pressures at the exit of a given reactor A in operation of first epoxidation subzone.

According to a first preferred embodiment of the present invention, the epoxidation zone according to (ii) consists of the first epoxidation subzone.

According to a second preferred embodiment of the present invention, the epoxidation zone according to (ii) additionally comprises a second epoxidation subzone consisting of one or more epoxidation reactors B wherein, if the second epoxidation subzone comprises two or more epoxidation reactors B, the two or more epoxidation reactors B are arranged in parallel, wherein the second epoxidation subzone is arranged downstream of the first epoxidation subzone. In this case, it is preferred that in (ii), the effluent stream obtained from the first epoxidation subzone, optionally after a suitable intermediate treatment, is passed into at least one of the epoxidation reactors B. It is possible, for example, that, while the effluent stream obtained from the first epoxidation subzone, optionally after a suitable intermediate treatment, is passed into at least one of the epoxidation reactors B, at least one of the reactors B is taken out of operation, for example for maintenance purposes and/or for regenerating the catalyst comprised in the at least one of the reactors B. If the second epoxidation subzone comprises two or more epoxidation reactors B, the reactors in operation are operated essentially identically so that in every epoxidation reactor B in operation, a given epoxidation condition is in the same range in every reactor. Generally, it is conceivable that in addition to the first epoxidation subzone and the second epoxidation subzone, the epoxidation zone according to (ii) comprises at least one further epoxidation subzone arranged downstream of the second epoxidation subzone. Preferably, according to the second preferred embodiment of the present invention, the epoxidation zone according to (ii) consists of the first epoxidation subzone and the second epoxidation subzone.

Preferably, the epoxidation conditions according to (ii) comprise a second epoxidation reaction pressure in the range of from 14 to 100 bar, preferably in the range of from 14.5 to 32 bar, more preferably in the range of from 15 to 25 bar. The second epoxidation reaction pressure is defined as the absolute pressure at the exit of the second epoxidation subzone. If the second epoxidation subzone comprises two or more epoxidation reactors B, the second epoxidation reaction pressure relates to the absolute pressures at the exit of a given reactor B in operation of second epoxidation subzone.

Preferably, the epoxidation conditions according to (ii) comprise an epoxidation catalyst loading in the second epoxidation subzone in the range of from 0.001 to 0.5 $h^{-1}$, more preferably in the range of from 0.005 to 0.3 $h^{-1}$, more preferably in the range of from 0.01 to 0.2 $h^{-1}$, wherein the epoxidation catalyst loading is defined as the ratio of the mass flow rate in kg/h of hydrogen peroxide contained in the feed stream passed into the second epoxidation subzone relative to the amount in kg of epoxidation catalyst comprising a titanium zeolite comprised in the second epoxidation subzone according to (ii).

Preferably, the temperature of the reaction mixture in the second epoxidation reaction subzone is not adjusted by passing a heat transfer medium through a jacket of the one or more epoxidation reactors B. More preferably, the second epoxidation subzone is an essentially adiabatic epoxidation subzone. More preferably, the second epoxidation subzone is an adiabatic epoxidation subzone.

The stream provided in (i) comprises an organic solvent, which is preferably an organic epoxidation solvent, more preferably one or more of methanol, acetonitrile, tert-butanol, propionitrile, more preferably one or more of methanol, acetonitrile.

Additions to the Effluent Stream and Epoxidation Catalyst

Preferably, the stream provided in (i), optionally the reaction mixture obtained in (ii) and optionally the effluent stream removed in (iii) additionally comprise at least one potassium salt, wherein the at least one potassium salt is selected from the group consisting of at least one inorganic potassium salt, at least one organic potassium salt, and combinations of at least one inorganic potassium salt and at least one organic potassium salt.

Preferably, the at least one potassium salt is selected from the group consisting of at least one inorganic potassium salt selected from the group consisting of potassium hydroxide, potassium halides, potassium nitrate, potassium sulfate, potassium hydrogen sulfate, potassium perchlorate, potassium salts of a phosphorus oxyacid, at least one organic potassium salt selected from the group consisting of potassium salts of aliphatic saturated monocarboxylic acids preferably having 1, 2, 3, 4, 5 or 6 carbon atoms, potassium carbonate, and potassium hydrogen carbonate, and a combination of at least one of the at least one inorganic potassium salts and at least one of the at least one organic potassium salts.

More preferably, the at least one potassium salt is selected from the group consisting of at least one inorganic potassium salt selected from the group consisting of potassium hydroxide, potassium chloride, potassium nitrate, potassium hydrogen phosphate, potassium dihydrogen phosphate, at least one organic potassium salt selected from the group consisting of potassium formate, potassium acetate, potassium carbonate, and potassium hydrogen carbonate, and a combination of at least one of the at least one inorganic potassium salts and at least one of the at least one organic potassium salts. More preferably, the at least one potassium salt comprises at least one of potassium dihydrogen phosphate, dipotassium hydrogen phosphate, or potassium formate.

The titanium zeolite comprised in the epoxidation catalyst is preferably a titanium zeolite having ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YUG, ZON framework structure or a mixed structure of two or more of these framework structures, more preferably a titanium zeolite having an MFI framework structure, an MEL framework structure, an MWW framework structure, an ITQ framework structure, a BEA framework structure, a MOR framework structure, or a mixed structure of two or more of these framework structures, more preferably an MFI framework structure, or an MWW framework structure.

The epoxidation catalyst comprising a titanium zeolite can be employed in every conceivable form, including a powder, a micropowder, preferably a spray-powder, as a molding comprising a powder, or as a molding comprising a micropowder, preferably a spray-powder. Preferably, the catalyst comprising the titanium zeolite is employed as a molding comprising a powder or a micropowder, preferably a spray-powder, more preferably as a molding comprising a micropowder, preferably a spray-powder. More preferably, the catalyst comprising the titanium zeolite is present in the epoxidation zone as a molding, preferably as fluidized-bed catalyst or a fixed-bed catalyst, more preferably as a fixed-bed catalyst.

In a first preferred embodiment, the titanium zeolite comprised in the epoxidation catalyst is a titanium zeolite having an MFI framework structure, preferably TS-1. Preferably, the titanium zeolite comprised in the epoxidation catalyst is a titanium zeolite having framework type MFI, preferably TS-1, the organic solvent comprises methanol and the stream provided in (i), optionally the reaction mixture obtained in (ii) and optionally the effluent stream removed in (iii) preferably comprise at least one potassium salt, more preferably at least one inorganic potassium salt, which preferably comprises at least one of potassium dihydrogen phosphate or dipotassium hydrogen phosphate.

Therefore, the present invention also relates to a process for preparing propylene oxide, comprising
 (i) providing a stream comprising propene, hydrogen peroxide or a source of hydrogen peroxide, water, and an organic solvent which comprises methanol;
 (ii) passing the liquid feed stream provided in (i) into an epoxidation zone comprising an epoxidation catalyst comprising a titanium zeolite which has an MFI framework structure, preferably TS-1, and subjecting the liquid feed stream to epoxidation reaction conditions in the epoxidation zone, obtaining a reaction mixture comprising propene, propylene oxide, water, and the organic solvent;
 (iii) removing an effluent stream from the epoxidation zone, the effluent stream comprising propylene oxide, water, organic solvent, and propene;
 (iv) separating propene from the effluent stream by distillation, comprising
  (iv.1) subjecting the effluent stream to distillation conditions in a distillation unit, obtaining a gaseous top stream S0 enriched in propene compared to the effluent stream subjected to distillation conditions, and a liquid bottoms stream S01 enriched in propylene oxide, water and organic solvent compared to the effluent stream subjected to distillation conditions;
  (iv.2) returning a condensed portion of the stream S0 to an upper part of the distillation unit,
 wherein the stream provided in (i), optionally the reaction mixture obtained in (ii) and optionally the effluent stream removed in (iii) preferably comprise at least one potassium salt, preferably at least one inorganic potassium salt, which preferably comprises at least one of potassium dihydrogen phosphate or dipotassium hydrogen phosphate.

In a second preferred embodiment, the titanium zeolite, preferably the titanium zeolite having an MWW framework structure, comprises at least one of Al, B, Zr, V, Nb, Ta, Cr, Mo, W, Mn, Fe, Co, Ni, Zn, Ga, Ge, In, Sn, Pb, Pd, Pt, Au, preferably at least one of B, Zr, V, Nb, Ta, Cr, Mo, W, Mn, Fe, Co, Ni, Zn, Ga, Ge, In, Sn, Pb, Pd, Pt, Au, more preferably Zn.

Preferably, the titanium zeolite is an aluminum-free zeolitic material of MWW framework structure, containing titanium, preferably in an amount of from 0.5 to 5 weight-%, more preferably from 1 to 2 weight-%, calculated as elemental titanium and based on the total weight of the titanium containing zeolite, and containing zinc, preferably in an amount of from 0.5 to 5 weight-%, preferably from 1 to 2 weight-%, calculated as elemental zinc and based on the total weight of the fresh, i.e. unused, titanium containing zeolite. The term "aluminum-free" in the context of the present invention refers to an embodiment according to which the aluminum content of the zeolitic material is 0.05 weight-ppm at most, preferably 0.03 weight-ppm at most, more preferably 0.02 weight-ppm at most, based on the total weight of zeolitic material. The weight-%-values refer to an embodiment according to which the zeolitic material is in dry state, preferably after drying for at least ten hours at 80° C. at a pressure of less than 1013.25 hPa.

More preferably, the titanium zeolite comprised in the epoxidation catalyst is a titanium zeolite of MWW framework structure, which is preferably aluminum-free and comprises zinc, the organic solvent is acetonitrile and the stream provided in (i), optionally the reaction mixture obtained in (ii) and optionally the effluent stream removed in (iii) preferably comprise at least one potassium salt, preferably at least one organic potassium salt, which preferably comprises at least potassium formate.

Therefore, the present invention also relates to a process for preparing propylene oxide, comprising
 (i) providing a stream comprising propene, hydrogen peroxide or a source of hydrogen peroxide, water, and an organic solvent which comprises acetonitrile;
 (ii) passing the liquid feed stream provided in (i) into an epoxidation zone comprising an epoxidation catalyst comprising a titanium zeolite which is a titanium zeolite of MWW framework structure, which is preferably aluminum-free and comprises zinc, and subjecting the liquid feed stream to epoxidation reaction conditions in the epoxidation zone, obtaining a reaction mixture comprising propene, propylene oxide, water, and the organic solvent;
 (iii) removing an effluent stream from the epoxidation zone, the effluent stream comprising propylene oxide, water, organic solvent, and propene;
 (iv) separating propene from the effluent stream by distillation, comprising
  (iv.1) subjecting the effluent stream to distillation conditions in a distillation unit, obtaining a gaseous top stream S0 enriched in propene compared to the effluent stream subjected to distillation conditions, and a liquid bottoms stream S01 enriched in propylene oxide, water and organic solvent compared to the effluent stream subjected to distillation conditions;
  (iv.2) returning a condensed portion of the stream S0 to an upper part of the distillation unit,
 wherein the stream provided in (i), optionally the reaction mixture obtained in (ii) and optionally the effluent stream removed in (iii) preferably comprise at least one potassium salt, preferably at least one organic potassium salt, which preferably comprises at least potassium formate.

The stream comprising propene, optionally propane, hydrogen peroxide or a source of hydrogen peroxide, water, an organic solvent and optionally at least one potassium salt provided in (i) is preferably liquid.

Stream Provided in (i)

Generally, the stream comprising propene, hydrogen peroxide or a source of hydrogen peroxide, water, and an organic solvent; can be provided in (i) according to any conceivable method. Preferably, the stream comprising propene, hydrogen peroxide or a source of hydrogen peroxide, water, and an organic solvent provided in (i) is prepared from two or more streams. More preferably, the stream is provided in (i) by combining at least three individual streams wherein a first stream comprises hydrogen peroxide or a source of hydrogen peroxide, a second stream comprises propene and optionally propane and a third stream comprises the organic solvent and optionally water.

Preferably,—as described already above—the stream comprising propene additionally comprises propane wherein preferably at least 98 weight-%, more preferably at least 99 weight-%, more preferably at least 99.5 weight-%, more preferably at least 99.9 weight-% of the stream consist of propene and propane. Preferably, the weight ratio of propene relative to propane in the stream is at least 7:3. For example, commercially available propene can be employed which may be either a polymer grade propene or a chemical grade propene. Typically, polymer grade propene has a propene content in the range of from 99 to 99.8 weight-% and a propane content in the range of from 0.2 to 1 weight-%. Chemical grade propene typically has a propene content in the range of from 92 to 98 weight-% and a propane content in the range of from 2 to 8 weight-%. Preferably, a stream is employed having a propene content in the range of from 99 to 99.8 weight-% and a propane content in the range of from 0.2 to 1 weight-%.

The stream comprising hydrogen peroxide can be prepared according to every conceivable method. It is conceivable to obtain the stream comprising hydrogen peroxide by converting sulphuric acid into peroxodisulphuric acid by anodic oxidation with simultaneous evolution of hydrogen at the cathode. Hydrolysis of the peroxodisulphuric acid then leads via peroxomonosulphuric acid to hydrogen peroxide and sulphuric acid which is then recycled. The preparation of hydrogen peroxide from the elements is also conceivable. Depending on the specific preparation method, the stream comprising hydrogen peroxide can be, for example, an aqueous or an aqueous/methanolic hydrogen peroxide stream, preferably an aqueous hydrogen peroxide stream. In case an aqueous hydrogen peroxide feed is employed, the content of the stream with respect to hydrogen peroxide is usually in the range of from 3 to 85 weight-%, preferably from 25 to 75 weight-%, more preferably from 30 to 50 weight-%, such as from 30 to 40 weight-% or from 35 to 45 weight-% of from 40 to 50 weight-%. Preferably, at least 25 weight-%, more preferably at least 30 weight-%, more preferably at least 35 weight-% of the stream comprising hydrogen peroxide consist of water and hydrogen peroxide. Preferred ranges are from 30 to 80 weight-% or from 35 to 75 weight-% or from 40 to 70 weight-%.

According to the present invention, it is preferred to employ a stream comprising hydrogen peroxide which is obtained as crude hydrogen peroxide solution by extraction of a mixture which results from a process known as anthraquinone process by means of which virtually the entire world production of hydrogen peroxide is produced (see, e.g., Ullmann's Encyclopedia of Industrial Chemistry, 5th edition, volume A 13 (1989) pages 443-466) wherein a solution of an anthraquinone is used containing an alkyl group preferably having of from 2 to 10 carbon atoms, more preferably at least 5 carbon atoms such as 5 carbon atoms or 6 carbon atoms and where the solvent used usually consists of a mixture of two different solvents, whereby preferably none of the solvents is a nitrogen containing substance. This solution of the anthraquinone is usually referred to as the working solution. In this process, the hydrogen peroxide formed in the course of the anthraquinone process is generally separated by extraction from the respective working solution after a hydrogenation/re-oxidation cycle. Said extraction can be performed preferably with essentially pure water, and the crude aqueous hydrogen peroxide solution is obtained. While it is generally possible to further purify the thus obtained crude aqueous hydrogen peroxide solution by distillation, it is preferred, according to the present invention, to use such crude aqueous hydrogen peroxide solution which has not been subjected to purification by distillation. Further, it is generally possible to subject the crude aqueous hydrogen peroxide solution to a further extraction stage wherein a suitable extracting agent, preferably an organic solvent is used. More preferably, the organic solvent used for this further extraction stage is the same solvent which is used in the anthraquinone process. Preferably the extraction is performed using just one of the solvents in the working solution and most preferably using just the most nonpolar solvent of the working solution. In case the crude aqueous hydrogen peroxide solution is subjected to such further extraction stage, a so-called crude washed hydrogen peroxide solution is obtained. According to a preferred embodiment of the present invention, the crude washed hydrogen peroxide solution is used as hydrogen peroxide feed. The production of a crude solution is described, for example, in European patent application EP 1 122 249 A1. As to the term "essentially pure water", reference is made to paragraph 10, page 3 of EP 1 122 249 A1 which is incorporated by reference. The hydrogen peroxide can also be treated to remove trace metals, for example, as described in the WO 2015/049327 A1 before use.

It is conceivable that the hydrogen peroxide is prepared in situ in the epoxidation zone from hydrogen and oxygen, preferably in the presence of a suitable noble metal catalyst comprised in the epoxidation zone according to (b). A suitable noble metal catalyst preferably comprises one or more of palladium, platinum, silver, gold, rhodium, iridium, ruthenium and osmium. Preferably, the noble metal catalyst comprises palladium. The noble metal catalyst is preferably supported on a carrier, wherein the carrier preferably comprises one or more of $SiO_2$, $Al_2O_3$, $B_2O_3$, $GeO_2$, $Ga_2O_3$, $ZrO_2$, $TiO_2$, MgO, carbon and one or more zeolites, preferably one or more titanium zeolites. More preferably, the carrier comprises the epoxidation catalyst comprising a titanium zeolite. If hydrogen peroxide is prepared in the epoxidation zone according to (b) in situ from hydrogen and oxygen, the stream provided in (a) comprises propene and preferably propane, hydrogen, oxygen, water, and acetonitrile.

Depressurization

According to (iv), propene is separated from the effluent stream by distillation. Preferably, prior to (iv), the effluent stream removed according to (iii) is depressurized, preferably to a a pressure of from 0.5 to 2.8 bar, more preferably of from 0.6 to 2.5 bar, more preferably of from 0.8 to 1.5 bar. Generally, there is no specific restriction how the effluent stream is depressurized. Preferably, the effluent stream is depressurized into a flash drum. Preferably, from depressurizing the effluent stream, a gaseous stream and a liquid stream are obtained, wherein the gaseous and liquid streams are preferably passed separately to the distillation unit employed according to (iv), preferably to the same theoretical tray of the distillation unit employed according to (iv).

Stream S0

According to (iv.1), a gaseous top stream S0 is obtained, which is enriched in propene compared to the effluent stream subjected to distillation conditions. Generally, there is no specific restriction regarding the conditions at which S0 is taken off. Preferably, S0 removed from the distillation unit employed in (iv) has a pressure of from 0.5 to 2.8 bar, more preferably of from 0.6 to 2.5 bar, more preferably of from 0.8 to 1.5 bar and a temperature in the range of from −70 to −30° C., more preferably of from −60 to −40° C., more preferably of from −55 to −45° C.

Generally, the composition of the gaseous top stream S0 obtained in (i) is not subject to any specific restrictions provided that it is enriched in propene compared to the effluent stream subjected to distillation conditions. Preferably, at least 80 volume-%, more preferably at least 85 volume-%, more preferably at least 89 volume-% of S0 consist of propene. Preferably, S0 comprises at the outmost 0.1 weight-%, more preferably in the range of from 1 to 250 weight-ppm propylene oxide.

Condensed Portion of S0

Generally, there are no specific restrictions regarding where the condensed portion of stream S0 is returned according to (iv.2), provided that it is done to an upper part of the distillation unit. Preferably, the condensed portion of S0 is returned to an upper part of the distillation unit in (iv.2) at the top of the distillation unit or within the rectifying section of the distillation unit, more preferably at the top of the distillation unit.

Generally, no specific restriction exists how much of S0 is condensed and forms the condensed portion of the stream S0, which is returned to an upper part of the distillation unit according to (iv.2). It is generally conceivable to condense S0 completely or to condense only a portion of S0. Preferably, only a portion of S0 is condensed. More preferably, the portion of S0 which is condensed, resulting in a condensed portion of stream S0, is regulated so that the oxygen concentration in the uncondensed portion of the stream S0 is less than 10 vol.-%, preferably less than 7 vol.-%, most preferably less than 5 vol.-%.

Preferably, of from 50 to 90 weight-%, more preferably of from 60 to 85 weight-%, more preferably of from 65 to 80 weight-%, of S0, which form the condensed portion of S0, are returned to an upper part of the distillation unit in (iv.2).

Generally, no specific restriction exists how the condensed portion of the stream S0, which is returned to an upper part of the distillation unit according to (iv.2), is obtained. Preferably, condensing is achieved by compression to a pressure in the range of from 5 to 20 bar, more preferably in the range of from 10 to 19 bar, more preferably in the range of from 12 to 18 bar and adjusting the temperature to be in the range of from 20 to 50° C., more preferably from 25 to 40° C., more preferably from 32 to 38° C.

Generally, no further adjustment regarding pressure or temperature of the condensed portion of the stream S0 before its return to the distillation unit according to (iv.2) is necessary. Thus, it is conceivable that the condensed portion of S0, which is returned to an upper part of the distillation unit in (iv.2), has a temperature in the range of from 20 to 50° C., preferably in the range of from 30 to 40° C., more preferably in the range of from 32 to 38° C. The "condensed portion of S0" refers to a still compressed state, meaning the state of the stream to be returned before entering the distillation unit, i.e. having a pressure in the range of from 5 to 20 bar, more preferably in the range of from 10 to 19 bar, more preferably in the range of from 12 to 18 bar. At entrance into the distillation unit, the stream (the condensed portion of S0) flashes due to decompression thus resulting also in a decrease in temperature.

According to a preferred embodiment, the condensed portion of the stream S0 is heat exchanged with stream S0 prior to the return to an upper part of the distillation unit in (iv.2). Preferably, the temperature of the condensed portion of the stream S0 is decreased after compression and prior to the return to an upper part of the distillation unit in (iv.2) by heat exchange with stream S0 by 35 to 80 K, preferably by 45 to 65 K, more preferably by 55 to 65 K. "Heat exchange with stream S0" refers to the stream S0 having the temperature at which S0 is removed from the distillation unit employed in (iv). Preferably, the temperature of the condensed portion of S0 is at maximum adjusted to the temperature of stream S0 at its removal from the distillation unit employed in (iv). More preferably, the temperature of the condensed portion of S0 is adjusted at maximum to a temperature in the range of from −70 to −30° C., more preferably of from −60 to −40° C., more preferably of from −55 to −45° C.

According to (iv.1), the effluent stream removed in (iii) is subjected to distillation conditions in a distillation unit, obtaining a gaseous top stream S0 enriched in propene compared to the effluent stream subjected to distillation conditions, and a liquid bottoms stream S01 enriched in propylene oxide, water and organic solvent compared to the effluent stream subjected to distillation conditions.

Preferably, the process further comprises in addition to steps (i), (ii), (iii) and (iv)

(v) separating propylene oxide from S01, obtaining a stream S02, preferably as bottoms stream, which is enriched in organic solvent and water compared to S01.

Preferably, a distillation unit is employed for the separation in (v), which is preferably at least one distillation tower, more preferably one distillation tower, which has preferably of from 30 to 80, more preferably of from 40 to 60 theoretical trays and is preferably operated at a top pressure of from 0.2 to 2 bar, more preferably of from 0.4 to 1 bar and preferably at a bottoms temperature in the range of from 40 to 80° C., preferably of from 60 to 70° C.

Regarding step (v), no specific restrictions exist. Preferably, the separation is carried out so that at least 95 weight-% of S02 consist of organic solvent and water, wherein preferably, the weight ratio of organic solvent relative to water in the stream S02 is greater than 1:1. Preferably, S02 obtained as bottoms stream contains 100 weight-ppm, preferably 50 weight-ppm, at most of the propylene oxide, based on the weight of S02.

Preferably, in (v) a further stream S03 is obtained, preferably as top stream, comprising the propylene oxide and being depleted of organic solvent and water compared to S01. More preferably, the stream S03 obtained in (v), preferably as top stream, contains at least 90 weight-%, more preferably at least 95 weight-%, more preferably at least 98 weight-% of propylene oxide.

Preferably, S03 is split into at least two streams S03a and S03b, and S03a, which contains of from 70 to 90 weight-%, more preferably of from 80 to 85 weight-% of S03, is returned to the distillation unit employed in (v), preferably at the top of the distillation unit.

It is possible that the stream S03, more preferably the stream S03b, is subjected to further work-up steps described herein below.

It is conceivable that the process further comprises, in addition to steps (i), (ii), (iii), (iv) and (v)

(vi) separating propylene oxide from the stream S03 or the stream S03b, preferably from the stream S03b, obtaining a propylene oxide stream S04 being enriched in propylene oxide compared to the stream S03 obtained in (v).

Preferably, a distillation unit is employed for the separation in (vi), which is preferably at least one distillation tower, more preferably one distillation tower, which has preferably of from 30 to 80, more preferably of from 50 to 60 theoretical trays and is preferably operated at a top pressure of from 0.5 to 5 bar, more preferably of from 2 to 4 bar and preferably at a at a bottom temperature in the range of from 50 to 90° C., preferably of from 65 to 75° C.

It is conceivable that the propylene oxide stream S04 is removed from the distillation unit employed in (vi) in the upper part of the distillation unit, preferably as top stream. Preferably, the propylene oxide stream S04 obtained in (vi) contains at least 99.800 weight-%, more preferably at least 99.990 weight-%, more preferably at least 99.995 weight-%, more preferably at least 99.998 weight-%, propylene oxide.

It is possible that in (vi) a further stream S05 is obtained, preferably as bottoms stream, which is enriched in organic solvent and water compared to S02 and which preferably contains 50 weight-ppm at most of the propylene oxide, based on the weight of S05.

The process for preparing propylene oxide, especially the providing of a stream comprising propene, hydrogen peroxide or a source of hydrogen peroxide, water, and an organic solvent in (i), the passing of the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propylene oxide, water, and the organic solvent, is a continuous process.

The present invention is further illustrated by the following set of embodiments and combinations of embodiments resulting from the given dependencies and back-references.

1. A process for preparing propylene oxide, comprising
    (i) providing a stream comprising propene, hydrogen peroxide or a source of hydrogen peroxide, water, and an organic solvent;
    (ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propylene oxide, water, and the organic solvent;
    (iii) removing an effluent stream from the epoxidation zone, the effluent stream comprising propylene oxide, water, organic solvent, and propene;
    (iv) separating propene from the effluent stream by distillation, comprising
        (iv.1) subjecting the effluent stream to distillation conditions in a distillation unit, obtaining a gaseous top stream S0 enriched in propene compared to the effluent stream subjected to distillation conditions, and a liquid bottoms stream S01 enriched in propylene oxide, water and organic solvent compared to the effluent stream subjected to distillation conditions;
        (iv.2) returning a condensed portion of the stream S0 to an upper part of the distillation unit.
2. The process of embodiment 1, comprising
    (i) providing a stream comprising propene, propane, hydrogen peroxide or a source of hydrogen peroxide, water, and an organic solvent;
    (ii) passing the liquid feed stream provided in (i) into an epoxidation zone comprising an epoxidation catalyst comprising a titanium zeolite, and subjecting the liquid feed stream to epoxidation reaction conditions in the epoxidation zone, obtaining a reaction mixture comprising propene, propane, propylene oxide, water, and the organic solvent;
    (iii) removing an effluent stream from the epoxidation zone, the effluent stream comprising propylene oxide, water, organic solvent, propene, and propane;
    (iv) separating propene and propane from the effluent stream by distillation, comprising
        (iv.1) subjecting the effluent stream to distillation conditions in a distillation unit, obtaining a gaseous top stream S0 enriched in propene and propane compared to the effluent stream subjected to distillation conditions, and a liquid bottoms stream S01 enriched in propylene oxide, water and organic solvent compared to the effluent stream subjected to distillation conditions;
        (iv.2) returning a condensed portion of the stream S0 to an upper part of the distillation unit.
3. The process of embodiment 1 or 2, wherein at least 95 weight-%, preferably from 95 to 100 weight-%, more preferably from 98 to 100 weight-%, more preferably from 99 to 100 weight-%, of the effluent stream removed in (iii) consist of propylene oxide, the organic solvent, water, propene, oxygen, and optionally propane.
4. The process of any one of embodiments 1 to 3, wherein the effluent stream removed in (iii) comprises the propylene oxide in amount of from 5 to 20 weight-%, preferably from 8 to 18 weight-%, more preferably from 10 to 14 weight-%, based on the total weight of the effluent stream; the organic solvent in amount of from 60 to 75 weight-%, preferably from 65 to 70 weight-%, based on the total weight of the effluent stream; the water in amount of from 10 to 25 weight-%, preferably from 15 to 20 weight-%, based on the total weight of the effluent stream; the propene in amount of from 1 to 5 weight-%, preferably from 3 to 4.5 weight-%, based on the total weight of the effluent stream; oxygen in an amount of from 0.05 to 1 weight-%, preferably from 0.1 to 0.5 weight-%, based on the total weight of the effluent stream; and optionally the propane in amount of from 0.1 to 2 weight-%, preferably from 0.2 to 1 weight-%, based on the total weight of the effluent stream.
5. The process of any one of embodiments 1 to 4, wherein the distillation unit employed in (iv) is at least one distillation tower, preferably one distillation tower, wherein the distillation tower has from 3 to 50, preferably from 5 to 15, more preferably from 6 to 10, more preferably from 7 to 9, theoretical trays.
6. The process of any one of embodiments 1 to 5, wherein the rectifying section of the distillation unit consists of from 50 to 75%, preferably of from 60 to 65%, of the theoretical trays and the stripping section of the distillation unit consists of from 25 to 50%, preferably of from 35 to 40%, of the theoretical trays.
7. The process of any one of embodiments 1 to 6, wherein the distillation unit employed in (iv) is operated at a top pressure of from 0.5 to 2.8 bar, preferably of from 0.6 to 2.5 bar, more preferably of from 0.8 to 1.5 bar.
8. The process of any one of embodiments 1 to 7, wherein the distillation unit employed in (iv) is operated at a top temperature in the range of from −70 to −30° C., preferably of from −60 to −40° C., more preferably of from −55 to −45° C.
9. The process of any one of embodiments 1 to 8, wherein prior to (iv), the effluent stream removed according to (iii) is depressurized.
10. The process of embodiment 9, wherein from depressurizing the effluent stream, a gaseous stream and a liquid stream are obtained.

11. The process of embodiment 10, wherein the gaseous and liquid streams are passed separately to the distillation unit employed according to (iv), preferably to the same theoretical tray of the distillation unit employed according to (iv).
12. The process of any one of embodiments 1 to 11, wherein the stream comprising propene, hydrogen peroxide or a source of hydrogen peroxide, water, and an organic solvent provided in (i) is prepared from two or more streams.
13. The process of any one of embodiments 1 to 12, wherein S0 removed from the distillation unit employed in (iv) has a pressure of from 0.5 to 2.8 bar, preferably of from 0.6 to 2.5 bar, more preferably of from 0.8 to 1.5 bar and a temperature in the range of from −70 to −30° C., preferably of from −60 to −40° C., more preferably of from −55 to −45° C.
14. The process of any one of embodiments 1 to 13, wherein at least 80 volume-%, more preferably at least 85 volume-%, more preferably at least 89 volume-% of S0 consist of propene.
15. The process of any one of embodiments 1 to 14, wherein the portion of S0 which is condensed, resulting in a condensed portion of stream S0, is regulated so that the oxygen concentration in the uncondensed portion of the stream S0 is less than 10vol.-%, preferably less than 7 vol.-%, most preferably less than 5 vol.-%.
16. The process of any one of embodiments 1 to 15, wherein condensing is achieved by compression to a pressure in the range of from 5 to 20 bar, preferably in the range of from 10 to 19 bar, more preferably in the range of from 12 to 18 bar and adjusting the temperature to be in the range of from 20 to 50° C., preferably from 25 to 40° C., more preferably from 32 to 38° C.
17. The process of any one of embodiments 1 to 16, wherein of from 50 to 90 weight-%, preferably of from 60 to 85 weight-%, more preferably of from 65 to 80 weight-%, of S0, which form the condensed portion of S0, are returned to an upper part of the distillation unit in (iv.2).
18. The process of any one of embodiments 1 to 17, wherein the condensed portion of S0 is returned to an upper part of the distillation unit in (iv.2) at the top of the distillation unit or within the rectifying section of the distillation unit, preferably at the top of the distillation unit.
19. The process of any one of embodiments 1 to 18, wherein the condensed portion of S0, which is returned to an upper part of the distillation unit in (iv.2), has a temperature in the range of from 20 to 50° C., preferably in the range of from 30 to 40° C., more preferably in the range of from 32 to 38° C.
20. The process of any one of embodiments 1 to 19, wherein the condensed portion of the stream S0 is heat exchanged with stream S0 prior to the return to an upper part of the distillation unit in (iv.2).
21. The process of any one of embodiments 1 to 20, wherein the temperature of the condensed portion of the stream S0 is decreased after compression and prior to the return to an upper part of the distillation unit in (iv.2) by 35 to 80 K, preferably by 45 to 65 K, more preferably by 55 to 65 K.
22. The process of any one of embodiments 1 to 21, wherein the stream provided in (i), optionally the reaction mixture obtained in (ii) and optionally the effluent stream removed in (iii) additionally comprise at least one potassium salt, wherein the at least one potassium salt is selected from the group consisting of at least one inorganic potassium salt, at least one organic potassium salt, and combinations of at least one inorganic potassium salt and at least one organic potassium salt.
23. The process of embodiment 22, wherein the at least one potassium salt is selected from the group consisting of at least one inorganic potassium salt selected from the group consisting of potassium hydroxide, potassium halides, potassium nitrate, potassium sulfate, potassium hydrogen sulfate, potassium perchlorate, potassium salts of a phosphorus oxyacid, at least one organic potassium salt selected from the group consisting of potassium salts of aliphatic saturated monocarboxylic acids preferably having 1, 2, 3, 4, 5 or 6 carbon atoms, potassium carbonate, and potassium hydrogen carbonate, and a combination of at least one of the at least one inorganic potassium salts and at least one of the at least one organic potassium salts.
24. The process of embodiment 22 or 23 wherein the at least one potassium salt is selected from the group consisting of at least one inorganic potassium salt selected from the group consisting of potassium hydroxide, potassium chloride, potassium nitrate, potassium hydrogen phosphate, potassium dihydrogen phosphate, at least one organic potassium salt selected from the group consisting of potassium formate, potassium acetate, potassium carbonate, and potassium hydrogen carbonate, and a combination of at least one of the at least one inorganic potassium salts and at least one of the at least one organic potassium salts.
25. The process of any one of embodiments 22 to 24, wherein the at least one potassium salt comprises at least one of potassium dihydrogen phosphate, dipotassium hydrogen phosphate, or potassium formate.
26. The process of any one of embodiments 1 to 25, wherein the organic solvent is an organic epoxidation solvent, and is preferably one or more of methanol, acetonitrile, tert-butanol, propionitrile, more preferably one or more of methanol, acetonitrile.
27. The process of any one of embodiments 1 to 26, wherein the titanium zeolite comprised in the epoxidation catalyst is a titanium zeolite having ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YUG, ZON framework structure or a mixed structure of two or more of these framework structures, preferably a titanium zeolite having an MFI framework structure, an MEL framework structure, an MWW framework structure, an ITQ framework structure, a BEA framework structure, a MOR framework structure, or a mixed structure of two or more of these framework structures, preferably an MFI framework structure, or an MWW framework structure.

28. The process of any one of embodiments 1 to 27, wherein the titanium zeolite comprised in the epoxidation catalyst is a titanium zeolite having an MFI framework structure, preferably TS-1.
29. The process of any one of embodiments 1 to 28, wherein the titanium zeolite comprised in the epoxidation catalyst is a titanium zeolite having framework type MFI, preferably TS-1, the epoxidation solvent comprises methanol and the stream provided in (i), optionally the reaction mixture obtained in (ii) and optionally the effluent stream removed in (iii) preferably comprise at least one potassium salt, preferably at least one inorganic potassium salt, which preferably comprises at least one of potassium dihydrogen phosphate or dipotassium hydrogen phosphate.
30. The process of any one of embodiments 1 to 27, wherein the titanium zeolite, preferably the titanium zeolite having an MWW framework structure, comprises at least one of Al, B, Zr, V, Nb, Ta, Cr, Mo, W, Mn, Fe, Co, Ni, Zn, Ga, Ge, In, Sn, Pb, Pd, Pt, Au, preferably at least one of B, Zr V, Nb, Ta, Cr, Mo, W, Mn, Fe, Co,Ni, Zn, Ga, Ge, In, Sn, Pb, Pd, Pt, Au, more preferably Zn.
31. The process of any one of embodiments 1 to 27 or 30, wherein the titanium zeolite is an aluminum-free zeolitic material of MWW framework structure, containing titanium, preferably in an amount of from 0.5 to 5 weight-%, more preferably from 1 to 2 weight-%, calculated as elemental titanium and based on the total weight of the titanium containing zeolite, and containing zinc, preferably in an amount of from 0.5 to 5 weight-%, preferably from 1 to 2 weight-%, calculated as elemental zinc and based on the total weight of the titanium containing zeolite.
32. The process of any one of embodiments 1 to 27or 30to 31, wherein the titanium zeolite comprised in the epoxidation catalyst is a titanium zeolite of MWW framework structure, preferably being aluminum-free and comprising zinc, the organic solvent comprises acetonitrile and the stream provided in (i), optionally the reaction mixture obtained in (ii) and optionally the effluent stream removed in (iii) preferably comprise at least one potassium salt, preferably at least one organic potassium salt, which preferably comprises at least potassium formate.
33. The process of any one of embodiments 1 to 32, wherein the stream comprising propene, optionally propane, hydrogen peroxide or a source of hydrogen peroxide, water, an organic epoxidation solvent and optionally at least one potassium salt provided in (i) is liquid.
34. The process of any one of embodiments 1 to 33, which in addition to steps (i), (ii), (iii) and (iv), further comprises
    (v) separating propylene oxide from SO1, obtaining a stream S02, preferably as bottoms stream, which is enriched in organic solvent and water compared to SO1.
35. The process of embodiment 34, wherein a distillation unit is employed for the separation in (v), which is preferably at least one distillation tower, more preferably one distillation tower, which has preferably of from 30 to 80, more preferably of from 40 to 60 theoretical trays and is preferably operated at a top pressure of from 0.2 to 2 bar, more preferably of from 0.4 to 1 bar and preferably at a bottom temperature in the range of from 40 to 80° C., preferably of from 60 to 70° C.
36. The process of any one of embodiments 34 to 35, wherein at least 95 weight-% of S02 consist of organic solvent and water, wherein preferably, the weight ratio of organic solvent relative to water in the stream S02 is greater than 1:1.
37. The process of any one of embodiments 34 to 36, wherein S02 obtained as bottoms stream contains 100 weight-ppm, preferably 50 weight-ppm, at most of the propylene oxide, based on the weight of S02.
38. The process of any one of embodiments 34 to 36, wherein in (v) a further stream S03 is obtained, preferably as top stream, comprising the propylene oxide and being depleted of organic solvent and water compared to S01.
39. The process of embodiment 38, Wherein the stream S03 obtained in (v), preferably as top stream, contains at least 90 weight-%, more preferably at least 95 weight-%, more preferably at least 98 weight-% of propylene oxide.
40. The process of embodiment 38 or 39, wherein S03 is split into at least two streams S03a and S03b, and S03a, which contains of from 70 to 90weight-%, more preferably of from 80 to 85 weight-% of S03, is returned to the distillation unit employed in (v), preferably at the top of the distillation unit.
41. The process of any one of embodiments 38 to 40, which in addition to steps (i), (iii), (iv) and (v), further comprises
    (vi) separating propylene oxide from the stream S03 or the stream S03b, preferably from the stream S03b, obtaining a propylene oxide stream S04 being enriched in propylene oxide compared to the stream S03 obtained in (v).
42. The process of embodiment 41, wherein a distillation unit is employed for the separation in (vi), which is preferably at least one distillation tower, more preferably one distillation tower, which has preferably of from 30 to 80, more preferably of from 50 to 60 theoretical trays and is preferably operated at a top pressure of from 0.5 to 5 bar, more preferably of from 2 to 4 bar and preferably at a at a bottom temperature in the range of from 50 to 90° C., preferably of from 65 to 75° C.
43. The process of embodiment 41 or 42, wherein the propylene oxide stream S04 is removed from the distillation unit employed in (vi) in the upper part of the distillation unit, preferably as top stream.
44. The process of any one of embodiments 41 to 43, wherein the propylene oxide stream S04 obtained in (vi) contains at least 99.800 weight-%, more preferably at least 99.990 weight-%, more preferably at least 99.995 weight-%, more preferably at least 99.998 weight-%, propylene oxide.
45. The process of any one of embodiments 41 to 44, wherein in (vi) a further stream S05 is obtained, preferably as bottoms stream, which is enriched in organic solvent and water compared to S02 and which preferably contains 50 weight-ppm at most of the propylene oxide, based on the weight of S05.
46. The process of any one of embodiments 1 to 45, which is a continuous process.

The present invention is further illustrated by the following reference examples, comparative examples, and examples.

EXAMPLES

Reference Example 1: Preparation of a Catalyst Comprising a Titanium Zeolite Having Framework Type MWW

1.1 Preparation of Boron Containing Zeolite of Structure MWW (BMWW)

A 2 m$^3$ stirred tank reactor was first loaded with 470.4 kg of deionized water. After starting the stirrer at 70 rpm, boric acid (162.5 kg) was added and the suspension was stirred for 3 h. Subsequently, piperidine (272.5 kg) was added at once causing the temperature to rise from 28° C. to 46° C. To this solution colloidal silica (Ludox® AS040, 392.0 kg) was added. The reactor was then slowly heated to 170° C. within 5 hours and then kept at this temperature under stirring for 120 hours. The maximum pressure during the reaction was 9.3 bar. Afterwards the reactor was cooled down to 50° C. The gel obtained had a pH of 11.3 and a viscosity of 15 mPa·s at 20° C. The gel was then filtered and the filter cake washed with deionized water until the conductivity of the washings was below 500 microSiemens/cm. The filter cake was then suspended in deionized water and the suspension was spray-dried at 235° C. using nitrogen as the carrier gas. The white powder obtained (174.3 kg) contained 3.5 weight-% water. This white powder was then calcined at 650° C. in a rotary kiln to give 138.2 kg of boron containing zeolite of structure type MWW (BMWW) as a white powder.

1.2 Deboronation of BMWW with Water

A 5 m$^3$ stirred tank reactor was loaded with 125 kg of the BMWW obtained according to the previous step 1.1 and 3750 kg of deionized water. The reactor was then slowly heated to 100° C. within 1 hour under stirring at 70 rpm, and then kept at this temperature for 20 hours and finally cooled to a temperature below 50° C. before it was filtered. The filter cake was then washed with deionized water until the washings had conductivity below 15 microSiemens/cm. The filter cake was then dried for 6 hours under a nitrogen stream. The filter cake was then removed and suspended in 850 kg of deionized water. This suspension was then spray-dried at 235° C. using nitrogen as the carrier gas. The spray dried material weighed 118.5 kg and contained 42.5 weight-% Si, 0.06 weight-% B and 0.23 weight-% C (total organic carbon, TOC).

1.3 Preparation of Titanium Containing Zeolite of Structure Type MWW (TiMWW)

A 2 m$^3$ stirred tank reactor was first loaded with 111.2 kg of the spray-dried material from the previous step 1.2. In a separate 2 m$^3$ stirred tank reactor were placed 400 kg of deionized water. After starting the stirrer at 80 rpm, piperidine (244.0 kg) was added. After the addition of piperidine was finished the mixture was stirred for 5 minutes before tetrabutyl orthotitanate (22.4 kg) was added. The pipe through which the titanate was added was then flushed with 40 kg of deionized water. The mixture was then stirred for 1 hour before being added to the first stirred tank reactor containing the spray-dried powder under stirring (50 rpm). The reactor was then heated to 170° C. and kept at this temperature for 120 h before being cooled to 50° C. The maximum pressure during the reaction was 10.6 bar. The cooled suspension was then filtered and the filter cake was washed with deionized water until the washings had conductivity below 1300 microSiemens/cm and an approximately neutral pH value. The filter cake was then dried under a nitrogen stream for 6 hours. The filter cake containing about 80 weight-% of water was used directly for the next step. The filter cake from the previous step and 1000 kg of deionized water were filled in a 2 m$^3$ stirred tank reactor. Then 1900 kg of nitric acid (53 weight-% in water) were added under stirring at 70 rpm. The reactor was then heated to 100° C. and kept at this temperature for 20 hours before being cooled to 50° C. The suspension obtained was then filtered and the filter cake was washed with deionized water until the conductivity was below 10 microSiemens/cm and the washings were approximately neutral. Subsequently the filter cake was dried under a stream of nitrogen for 6 hours. This filter cake was then suspended in water and spray-dried at 235° C. using nitrogen as the carrier gas. 96 kg of a spray-dried powder were obtained. This material was then calcined in a rotary kiln at 650° C. 84 kg of titanium zeolite of structure type MWW (TiMWW) were obtained as a powder containing 43 weight-% Si, 2.0 weight-% Ti and 0.2 weight-% C (TOC). The pore volume determined by Hg-porosimetry according to DIN 66133 was 7.3 ml/g and the BET surface area determined according to DIN 66131 was 467 m$^2$/g.

1.4 Preparation of a Zinc Containing TiMWW (ZnTiMWW) by Impregnation a) In a vessel equipped with a reflux condenser, a solution of 981 kg deionized water and 6.0 kg zinc acetate dihydrate was prepared within 30 min. Under stirring (40 r.p.m.), 32.7 kg of the calcined Ti-MWW material obtained according to 1.3 above were suspended. Subsequently, the vessel was closed and the reflux condenser put into operation. The stirring rate was increased to 70 r.p.m.

b) In a vessel equipped with a reflux condenser, a solution of 585 kg deionized water and 3.58 kg zinc acetate dihydrate was prepared within 30 min. Under stirring (40 r.p.m.), 19.5 kg of the calcined Ti-MWW material obtained according to 1.3 above were suspended. Subsequently, the vessel was closed and the reflux condenser put into operation. The stirring rate was increased to 70 r.p.m.

In all batches a) and b), the mixture in the vessel was heated to 100° C. within 1 h and kept under reflux for 2 h at a stirring rate of 70 r.p.m. Then, the mixture was cooled within 2 h to a temperature of less than 50° C. For each batch a) and b), the cooled suspension was subjected to filtration, and the mother liquor was transferred to waste water discharge. The filter cake was washed five times with deionized water under a nitrogen pressure of 2.5 bar. After the last washing step, the filter cake was dried in a nitrogen stream for 10 h. In total 297 kg of nitrogen dried filter cake were obtained. The thus dried Zn-impregnated TiMWW material (ZnTiMWW), had a Si content of 42 weight-%, a Ti content of 1.8 weight-%, a Zn content of 1.3 weight-.%.

From 297 kg of the mixture of the filter cake obtained above, an aqueous suspension was prepared with deionized water, the suspension having a solid content of 15 weight-%. This suspension was subjected to spray-drying in a spray-tower with the following spray-drying conditions:

apparatus used: spray tower with one nozzle operation mode: nitrogen straight configuration: dehumidifier—filter—scrubber dosage: flexible-tube pump VF 10 (supplier: Verder) nozzle with a diameter of 4 mm (supplier: Niro)

filter material: Nomex® needle-felt 10 m$^2$

| | | Runtime/h | | | | |
|---|---|---|---|---|---|---|
| | | 0.5 | 1.5 | 2.5 | 3.5 | 4.5 |
| Flow rate gas/(kg/h) | | 550 | 550 | 550 | 550 | 550 |
| Temperature drying gas/° C. | spray tower (in) | 305 | 305 | 305 | 305 | 305 |
| | spray tower (out) | 151 | 151 | 151 | 151 | 151 |
| | Filter (in) | 140 | 137 | 130 | 127 | 126 |
| | Scrubber (in) | 110 | 110 | 110 | 108 | 105 |
| | Scrubber (out) | 14 | 14 | 15 | 15 | 15 |
| Differential pressure/mbar | spray tower | 3.1 | 3 | 3 | 2.8 | 2.9 |
| | Filter | 1.7 | 1.7 | 1.8 | 1.8 | 2.1 |
| | Scrubber | 3.8 | 4.1 | 4.2 | 4.2 | 4.2 |
| Pressure/mbar | spray tower | −1.03 | −1.2 | −0.9 | −0.9 | −1.1 |
| Nozzle gas | Flow rate kg/h | 23 | 23 | 23 | 23 | 23 |
| | Temperature/° C. | r.t.*) | r.t.*) | r.t.*) | r.t.*) | r.t.*) |
| | Pressure/bar | 2.5 | 2.5 | 2.5 | 2.5 | 2.5 |
| Spray-dried product | Temperature/° C. | r.t.*) | r.t.*) | r.t.*) | r.t.*) | r.t.*) |

*)room temperature

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening. The spray-dried material thus obtained had a Zn content of 1.4 weight-%, a Ti content of 1.7 weight-%, a Si content of 41 weight-%, and a TOC content of <0.5 weight-%. The spray-dried product was then subjected to calcination for 2 h at 650° C. under air in a rotary furnace, yielding 43.8 kg of calcined spray-dried ZnTiMWW. The calcined spray-dried material thus obtained had a Zn content of 1.3 weight-%, a Ti content of 1.8 weight-%, a Si content of 42.5 weight-%, and a C content of <0.1 weight-%. The bulk density of the calcined spray-dried ZnTiMWW was 90 g/l (gram/liter). The mesopores of the micropowder had an average pore diameter (4V/A) of 20.2 nm as determined by Hg porosimetry according to DIN 66133. The macropores of the micropowder had an average pore diameter (4V/A) of 67.6 nm as determined by Hg porosimetry according to DIN 66133. The micropores of the ZnTiMWW contained in the micropowder had an average pore diameter of 1.06 nm as determined by nitrogen adsorption according to DIN 66134 (Horward-Kawazoe method). The Dv10 value of the particles of the micropowder was 4.10 micrometers. The Dv50 value of the particles of the micropowder was 8.19 micrometers. The Dv90 value of the particles of the micropowder was 14.05 micrometers. The degree of crystallization determined via XRD was (77+/−10) %, the average crystallite size 35.0 nm+/−10%. It was found that the crystalline phase exhibits a pure MWW structure. No other crystalline titania phases such as anatase, rutile or brookite, or crystalline zinc silicate ($Zn_2SiO_4$) such as willemite could be detected.

1.5 Preparation of Moldings Containing ZnTiMWW and Silica Binder

Starting from the calcined spray-dried ZnTiMWW material obtained according to 1.4 above, a molding was prepared, dried, and calcined. Therefor, 12 batches were prepared, each starting from 3.5 kg of the calcined spray-dried ZnTiMWW material obtained above, 0.226 kg Walocel™ (Walocel MW 15000 GB, Wolff Cellulosics GmbH & Co. KG, Germany), 2.188 kg Ludox® AS-40 and 6.6 l deionized water, as follows:

3.5 kg ZnTiMWW and 0.226 kg Walocel were subjected to kneading in an edge mill for 5 min. Then, during further kneading, 2.188 kg Ludox were added continuously. After another 10 min, addition of 6 l of deionized water was started. After another 30 min, further 0.6 l of deionized water were added. After a total time of 50 min, the kneaded mass had become extrudable. Thereafter, the kneaded mass was subjected to extrusion under 65-80 bar wherein the extruder was cooled with water during the extrusion process. Per batch, the extrusion time was in the range of from 15 to 20 min. The power consumption per batch during extrusion was 2.4 A. A die head was employed allowing for producing cylindrical strands having a diameter of 1.7 mm. At the die head out outlet, the strands were not subjected to a cutting to length. The strands thus obtained were dried for 16 h at 120° C. in a drying chamber under air. In total (sum of the 12 batches), 56 kg white strands with a diameter of 1.7 mm were obtained. 56 kg of the dried strands were subjected to calcination in a rotary furnace at 550° C. for 1 h under air, yielding 52 kg calcined strands. Thereafter, the strands were sieved (mesh size 1.5 mm), and the yield, after sieving, was 50.0 kg. The thus obtained moldings exhibited a bulk density of 322 g/l (gram per liter) and had a Zn content of 1.1 weight-%, a Ti content of 1.4 weight-%, a Si content of 43 weight-%, and a C content of <0.1 weight-%. The mesopores of the micropowder had an average pore diameter (4V/A) of 20.9 nm as determined by Hg porosimetry according to DIN 66133. The macropores of the micropowder had an average pore diameter (4V/A) of 50.0 nm as determined by Hg porosimetry according to DIN 66133. The degree of crystallization determined via XRD was (70+/−10) %, the average crystallite size 32.5 nm+/−10%. The crush strength of the moldings as determined according to the method using a crush strength test machine Z2.5/TS01S was 4.4 N (standard deviation: 0.5 N). The minimum value found when testing the 10 samples was 3.5 N, the maximum value 5.1 N. In the $^{29}Si$ MAS NMR, after the curve had been deconvolved by the proper Gaussian-Lorentzian line shapes, six peaks were clearly observed. The $Q^3/Q^4$ ratio was found to be 2.2. The total amount of adsorbed water as determined according to Reference Example 6 of the molding was 6.9 weight-%. The Langmuir surface are determined via nitrogen adsorption at 77 K according to DIN 66133 was 518 $m^2/g$, the mulitpoint BET specific surface area determined via nitrogen adsorption at 77 K according to DIN 66133 was 373 $m^2/g$. The total intrusion volume determined according to Hg porosimetry according to DIN 66133 was 1.3 ml/g (milliliter/gram), the respective total pore area 100.2 $m^2/g$. It was found that the crystalline phase of the moldings exhibits a pure MWW structure. No other crystalline titania phases such as anatase, rutile or brookite, or crystalline zinc silicate ($Zn_2SiO_4$) such as willemite could be detected via XRD.

Starting from the calcined strands, a post-treatment stage was performed as follows: 1,000 kg deioinized water were filled in a vessel. Then, 50 kg of the calcined moldings were added. The vessel was closed (pressure-tight), and the obtained mixture was heated to a temperature of 145° C. within 1.5 h and kept at this temperature under autogenous pressure (about 3 bar) for 8 h. Then, the mixture was cooled for 2 h. The water-treated strands were subjected to filtration and washed with deionized water. The obtained strands were heated in a drying chamber under air within 1 h to a temperature of 120° C. and kept at this temperature for 16 h. Subsequently, the dried material was heated under air to a temperature of 450° C. within 5.5 h and kept at this temperature for 2 h. Thereafter, the strands were sieved (mesh size 1.5 mm), and the yield, after sieving, was 49.1 kg. The thus obtained water-treated moldings exhibited a bulk density of 332 g/l (gram per liter) and had a Zn content of 1.1 weight-%, a Ti content of 1.4 weight-%, a Si content of 42 weight-%, and a C content of <0.10 weight-%. The mesopores of the micropowder had an average pore diameter (4V/A) of 22.1 nm as determined by Hg porosimetry according to DIN 66133. The macropores of the micropowder had an average pore diameter (4V/A) of 52.0 nm as determined by Hg porosimetry according to DIN 66133. The degree of crystallization determined via XRD was (69+/−10) %, the average crystallite size 30.5 nm+/−10%. The crush strength of the moldings as determined according to the method using a crush strength test machine Z2.5/TS01S was 13.7 N (standard deviation: 2.5 N). The minimum value found when testing the 10 samples was 10.2 N, the maximum value 17.6 N. In the $^{29}$Si MAS NMR, after the curve had been deconvolved by the proper Gaussian-Lorentzian line shapes, six peaks were clearly observed. The $Q^3/Q^4$ ratio was found to be 1.39. The total amount of adsorbed water of the molding was 6.9 weight-%. The intensity ratio of the infrared band in the region of (3746+/−20) cm$^{-1}$ attributed to the free silanol groups, relative to the infrared band in the region of 3688+/−20 cm$^{-1}$ attributed to vicinal silanol groups was smaller than 1.4. The Langmuir surface are determined via nitrogen adsorption at 77 K according to DIN 66133 was 421 m$^2$/g, the multipoint BET specific surface area determined via nitrogen adsorption at 77 K according t DIN 66133 was 303 m$^2$/g. The total intrusion volume determined according to Hg porosimetry according to DIN 66133 was 1.3 ml/g (milliliter/gram), the respective total pore area 98.7 m$^2$/g. It was found that the crystalline phase of the moldings exhibits a pure MWW structure. No other crystalline titania phases such as anatase, rutile or brookite, or crystalline zinc silicate ($Zn_2SiO_4$) such as willemite could be detected via XRD.

Reference Example 2: Characterization of the Catalyst

Reference Example 2.1: Determination of Dv10, Dv50, and Dv90 Values 1.0 g of the micropowder is suspended in 100 g deionized water and stirred for 1 min. The sample was subjected to the measurement in an apparatus using the following parameters: Mastersizer S long bed version 2.15, ser. No. 33544-325; supplier: Malvern Instruments GmbH, Herrenberg, Germany: focal width 300 RF mm; beam length 10.00 mm; module MS017; shadowing 16.9%; dispersion model 3$$D; analysis model polydisperse correction none.

Reference Example 2.2: Determination of the Silanol Concentration of the Moldings of the Present Invention For the determination of the silanol concentration, the $^{29}$Si MAS NMR experiments were carried out at room temperature on a VARIAN Infinityplus-400 spectrometer using 5.0 mm $ZrO_2$ rotors. The $^{29}$Si MAS NMR spectra were collected at 79.5 MHz using a 1.9 μs π/4 (microsecond pi/4) pulse with 10 s recycle delay and 4000 scans. All $^{29}$Si spectra were recorded on samples spun at 6 kHz, and chemical shifts were referenced to 4,4-dimethyl-4-silapentane sulfonate sodium (DSS). For the determination of the silanol group concentration, a given $^{29}$Si MAS NMR spectrum is deconvolved by the proper Gaussian-Lorentzian line shapes. The concentration of the silanol groups with respect to the total number of Si atoms is obtained by integrating the deconvolved $^{29}$Si MAS NMR spectra.

Reference Example 2.3: Determination of the Crush Strength of the Moldings

The crush strength as referred to in the context of the present invention is to be understood as determined via a crush strength test machine Z2.5/TS01S, supplier Zwick GmbH & Co., D-89079 Ulm, Germany. As to fundamentals of this machine and its operation, reference is made to the respective instructions handbook "Register 1: Betriebsanleitung/Sicherheitshandbuch für die Material-Prüfmaschine Z2.5/TS01S", version 1.5, December 2001 by Zwick GmbH & Co. Technische Dokumentation, August-Nagel-Strasse 11, D-89079 Ulm, Germany. With said machine, a given strand is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min.

The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

Reference Example 2.4: $^{29}$Si Solid-state NMR Spectra Regarding $Q^3$ and $Q^4$ Structures The effect of the inventive water treatment on the molding related to $Q^3$ and $Q^4$ structures in the material was characterized by comparing the changes in $^{29}$Si solid-state NMR spectra under comparable conditions. All $^{29}$Si solid-state NMR experiments were performed using a Bruker Advance spectrometer with 300 MHz $^1$H Larmor frequency (Bruker Biospin, Germany). Samples were packed in 7 mm $ZrO_2$ rotors, and measured under 5 kHz Magic Angle Spinning at room temperature. $^{29}$Si direct polarization spectra were obtained using (pi/2)-pulse excitation with 5 microsecond pulse width, a $^{29}$Si carrier frequency corresponding to −65 ppm in the spectrum, and a scan recycle delay of 120 s. Signal was acquired for 25 ms under 45 kHz high-power proton decoupling, and accumulated over 10 to 17 hours. Spectra were processed using Bruker Topspin with 30 Hz exponential line broadening, manual phasing, and manual baseline correction over the full spectrum width. Spectra were referenced with the polymer Q8M8 as an external secondary standard, setting the resonance of the trimethylsilyl M group to 12.5 ppm. The spectra were then fitted with a set of Gaussian line shapes, according to the number of discernable resonances. Relating to the presently assessed spectra, 6 lines in total were used, accounting for the five distinct peak maxima (at approximately −118, −115, −113, −110 and −104 ppm) plus the clearly visible shoulder at −98 ppm. Fitting was performed using DMFit (Massiot et al., Magnetic Resonance in Chemistry, 40 (2002) pp 70-76). Peaks were manually set at the visible peak maxima or shoulder. Both peak position and line width were then left unrestrained, i.e., fit peaks were not fixed at a certain position. The fitting outcome was numerically stable, i.e., distortions in the initial fit setup as described above did lead to similar results. The fitted peak areas were further used normalized as done by DMFit. After the water treatment of the invention, a decrease of signal intensity at the left hand side of the spectrum was observed, a region that includes $Q^3$ silanol structures (here especially: around and above −104 ppm, i.e. "left" of −104 ppm). Further, an increase of signal at the right hand side of the spectrum (here: below −110 ppm, i.e. "right" of −110 ppm) was observed, which region comprises $Q^4$ structures exclusively. For the quantification of spectrum changes, a ratio was calculated that reflects changes in the peak areas "left hand" and "right hand", as follows. The six peaks were labeled with 1, 2, 3, 4, 5, and 6, and the ratio Q was calculated with the formula $100*\{[a_1+a_2]/[a_4+a_5+a_6]\}/a_3$. In this formula, $a_{i, i=1 \ldots 6}$ represents the area of the fitted peak to which this number was attributed.

Reference Example 2.5: Water Adsorption/Desorption—Water Uptake

The water adsorption/desorption isotherms measurements were performed on a VTI SA instrument from TA Instruments following a step-isotherm program. The experiment consisted of a run or a series of runs performed on a sample material that has been placed on the microbalance pan inside of the instrument. Before the measurement were started, the residual moisture of the sample was removed by heating the sample to 100° C. (heating ramp of 5° C./min) and holding it for 6 h under a $N_2$ flow. After the drying program, the temperature in the cell was decreased to 25° C. and kept isothermal during the measurements. The microbalance was calibrated, and the weight of the dried sample was balanced (maximum mass deviation 0.01 weight-%). Water uptake by the sample was measured as the increase in weight over that of the dry sample. First, an adsorption curve was measured by increasing the relative humidity (RH) (expressed as weight-% water in the atmosphere inside of the cell) to which the samples was exposed and measuring the water uptake by the sample at equilibrium. The RH was increased with a step of 10 weight-% from 5 to 85% and at each step the system controlled the RH and monitored the sample weight until reaching the equilibrium conditions and recording the weight uptake. The total adsorbed water amount by the sample was taken after the sample was exposed to the 85 weight-% RH. During the desorption measurement the RH was decreased from 85 weight-% to 5 weight-% with a step of 10% and the change in the weight of the sample (water uptake) was monitored and recorded.

Reference Example 2.6: FT-IR Measurements

The FT-IR (Fourier-Transformed-Infrared) measurements were performed on a Nicolet 6700 spectrometer. The molding was powdered and then pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 $cm^{-1}$ at a resolution of 2 $cm^{-1}$. The obtained spectra are represented in a plot having on the x axis the wavenumber ($cm^{-1}$) and on the y axis the absorbance (arbitrary units, a.u.). For the quantitative determination of the peak heights and the ratio between these peaks a baseline correction was carried out. Changes in the 3000-3900 $cm^{-1}$ region were analyzed and for comparing multiple samples, as reference the band at 1880±5 $cm^{-1}$ was taken.

Reference Example 2.7: Determination of Crystallinity Via XRD

The crystallinity of the zeolitic materials according to the present invention were determined by XRD analysis. The data were collected using a standard Bragg-Brentano diffractometer with a Cu—X-ray source and an energy dispersive point detector. The angular range of 2° to 70° (2 theta) was scanned with a step size of 0.02°, while the variable divergence slit was set to a constant illuminated sample length of 20 mm. The data were then analyzed using TOPAS V4 software, wherein the sharp diffraction peaks were modeled using a Pawley fit containing a unit cell with the following starting parameters: a=14.4 Angstrom (1 Angstrom=$10^{-10}$ m) and c=25.2 Angstrom in the space group P6/mmm. These were refined to fit the data. Independent peaks were inserted at the following positions. 8.4°, 22.4°, 28.2° and 43°. These were used to describe the amorphous content. The crystalline content describes the intensity of the crystalline signal to the total scattered intensity. Included in the model were also a linear background, Lorentz and polarization corrections, lattice parameters, space group and crystallite size.

Reference Example 3: Epoxidation Process

A main reactor was a vertically mounted tube-bundle reactor with 3 tubes (length of the tubes: 12 m, internal tube diameter: 38 mm), each tube being equipped with an axially placed multipoint thermocouple each with 10 measuring points encased in a suitable thermowell with an external diameter of 18 mm. Each tube was charged with 3.2 kg of the ZnTiMWW catalyst moldings as prepared according to Reference Example 1 (post-treated moldings). Free space eventually remaining was filled with high purity aluminum oxide spheres (Denstone® 99, diameter of 5-6 mm). The heat of reaction was removed by circulating a thermostatized heat transfer medium (water/glycol mixture) on the shell side in co-current to the feed. The flow rate of the heat transfer medium was adjusted so that the temperature difference between entrance and exit of the cooling medium did not exceed 1° C. The reaction temperature referred to hereinbelow, also referred to as TR, was defined as the temperature of the heat transfer medium entering the reactor shell. At the reactor exit, the pressure was controlled by a pressure regulator and kept constant at 20 bar(abs). The output stream leaving the main reactor was sampled every 20 minutes in order to determine the hydrogen peroxide concentration using the titanyl sulfate method and to calculate the hydrogen peroxide conversion. The hydrogen peroxide conversion was defined as $100\times(1-m_{out}/m_{in})$ wherein $m_{in}$ is the molar flow rate of $H_2O_2$ in the reactor feed and $m_{out}$ is the molar flow rate of $H_2O_2$ in the reactor outlet. Based on the respectively obtained hydrogen peroxide conversion values, the inlet temperature of the heat transfer medium was adjusted in order to keep the hydrogen peroxide conversion essentially constant in the range of from 95 to 97%. The inlet temperature of the heat transfer medium was set at 30° C. at the start of a given run with a fresh batch of the epoxidation catalyst and was increased, if necessary, to maintain the hydrogen peroxide conversion in the mentioned range. The required temperature increase was usually less than 0.1 K/d. The output stream leaving the main epoxidation reactor was passed through a heat exchanging unit that regulates the temperature to 40° C. The stream leaving the heat exchanging unit was fed to the finishing reactor.

The finishing reactor was an upright fixed bed reactor operated adiabatically and fed from below. In this context, the term "adiabatic" refers to an operation mode according to which no active cooling is carried out and according to which the finishing reactor is suitably insulated in order to minimize heat losses. The finishing reactor had a length of 4 m and a diameter of 100 mm. The reactor was filled with 4.5 kg of the same epoxidation catalyst which was used in the main epoxidation reactor. Spare space was filled with high purity aluminum oxide spheres (Denstone® 99, diameter of 3 mm). The operating pressure of the finishing reactor was 10 bar which was kept constant by a suitable pressure regulator at the reactor exit. The output of the finishing reactor was sampled every 20 min in order to determine the hydrogen peroxide concentration using the titanyl sulfate method. The effluent of the finishing reactor was then used as the feed for the distillations described in the examples below.

The main reactor was fed from below with 101 kg/h of a liquid monophasic stream with the following composition: 63.7 wt.-% acetonitrile, 12.7 wt.-% propene, 7.1 wt.-% $H_2O_2$, 14.8 wt.-% water and 150 wppm potassium formate. The balance was propane and high boiling organic impurities. The temperature of the feed stream to the main reactor was adjusted to approximately 30° C. before being fed to the main reactor.

The epoxidation was performed in a continuous manner. The effluent stream downstream of the pressure control valve of the finishing reactor was metered using a suitable mass-flow-meter and samples were taken at regular intervals for analysis. Organic components and $O_2$ were analyzed in two separate gas-chromatographs. The hydrogen peroxide content was determined colorimetrically using the titanyl sulfate method. Effluent stream comprised 63.7 weight-% acetonitrile, 18.6 weight-% water, 11.8 weight-% propylene oxide, 4.0 weight-% propene, 0.14 weight-% propylene glycol, 0.5 weight-% propane, 0.03 weight-% oxygen, and 0.018 weight-% $H_2O_2$. The balance consists of a mixture of high-boiling organic by-products and impurities.

COMPARATIVE AND INVENTIVE EXAMPLES 1.1 Simulations

The data of the Comparative and the inventive Examples were obtained from simulations with program package AspenONE V8.6 (company Aspentech). The thermodynamic data used in the simulations was taken from the Dortmunder Datenbank (http://www.ddbst.com/). Only electrically ran compressors and the steam driven boilers have been considered as energy consumers. Energy costs associated with cooling water (energy for cooling water pumps) have been disregarded since they were negligible when compared to the other energy costs. The comparison of the results was carried out based on the calculated thermal and electric energy demands in MW respectively.

Comparative Example 1

Effluent stream of the finishing reactor, which represented the feed stream (F) for all the examples, was kept constant with respect to mass flow as well as composition. For the calculation, the high-boiler was taken as consisting exclusively of propylene glycol, which is anyhow the major component. The mass flow of stream F was set to 100 t/h. The stream F was liquid, had a pressure of 1.1 bar and a temperature of 46.7° C.
The setup is shown in FIG. 1.

The following boundary conditions were set for all the calculations: 1) the concentration of propylene oxide in the distillate (stream T1, S0) was set at 70 weight-ppm; 2) the concentration of propene in the sump (stream B, S01) was set at 100 weight-ppm.

Stream R, used as washing fluid, contained 76.3 wt.-% acetonitrile, 22.3 wt.-% water, the balance being propylene glycol. This stream was fed to the top of the tower as a liquid with a temperature of 10° C. and a flow rate of 32.4 t/h.

The distillation tower was operated at a top pressure of 1.0 bar and was calculated with 8 theoretical stages (including reboiler). The feed point of stream F was at stage 5 counted from the top.

Under these boundary conditions, stream T1 (S01), which consisted mostly of propene, propane and 02 had a mass flow rate of 4.65 t/h and a temperature of 11.3° C. (=temperature at the top of the tower). This stream was then compressed to 16.7 bar and cooled to 36.6° C. The bottom stream B (S01) was taken out with a temperature of 69.1° C.

Under these conditions the combined reboiler duty and electrical power for compression added up to 3.26 MW.

Comparative Example 2

The boundary conditions for this example were the same as for comparative example 1, but as a washing stream R an aqueous stream was used. This stream contained 98.7 wt.-% water the remainder being propylene glycol. The stream was fed to the top of the tower at 10° C. and with a mass flow rate of 49.6 t/h (since water is a poorer absorbent, more had to be used in order to fulfill the separation requirements). The top stream T1 (S0) had a temperature of 9.7° C. (=temperature at the top of the tower) and a flow rate of 4.8 t/h. This stream was then compressed to 16.7 bar and cooled to 36.6° C. The temperature of stream B (S01) was 68.9° C. Under these conditions the combined reboiler duty and electrical power for compression added up to 5.03 MW.

Example 1

Figure 2:
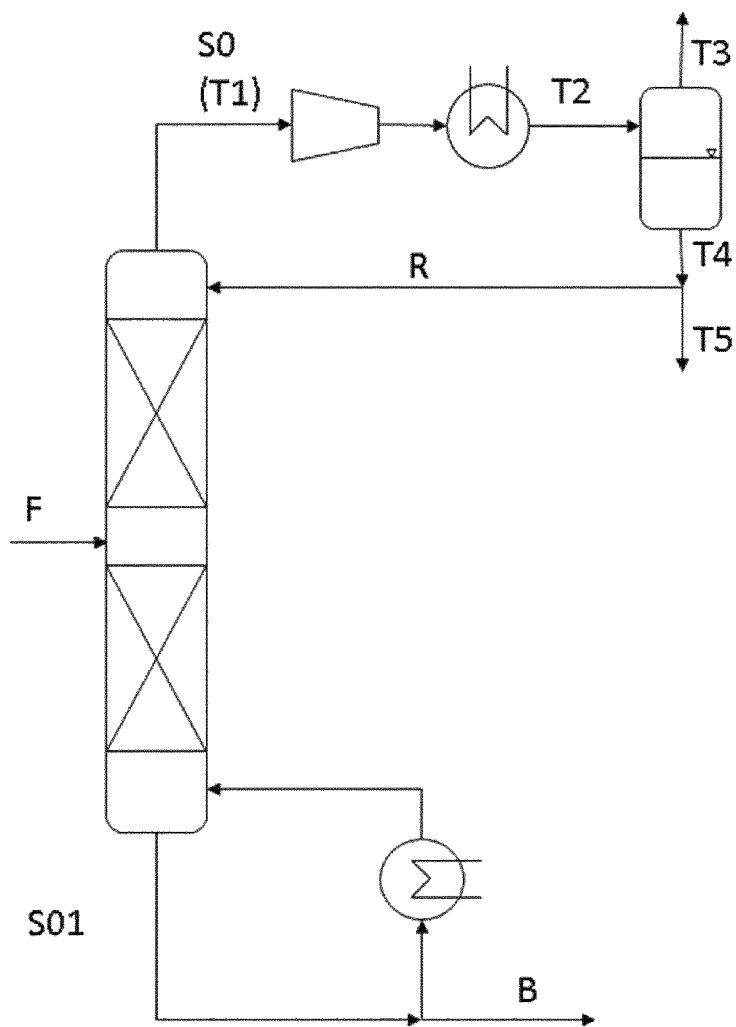

The boundary conditions of example 1 were the same as in comparative example 1, with the exception that no external washing stream was used. Instead, a condensed portion of S0, here a part of the liquefied top stream T4 obtained after compression, cooling and gas/liquid separation, was fed back to the top of the tower as a reflux stream. The setup is schematically shown in FIG. 2.

The temperature at the top of the tower was now −47.8° C. (=temperature of T1, S0). The mass flow rate of stream T1 (S0) was 19.0 t/h. This was compressed to 16.7 bar and cooled to 35.1° C., whereas most of the stream condensed. The resulting stream T2 was separated into a gaseous stream T3 and a liquid stream T4. From the liquid stream T4, 14.6 t/h were returned as stream R to the top of the distillation tower, where it flashed. The remainder of stream T4, stream T5 was discharged.

The temperature at the bottom of the tower was now 67.8° C. (=temperature B, S01). Under these conditions the combined reboiler duty and electrical power for compression added up to 3.13 MW and thus 4% lower than the energy required in the best comparative example (comp. example 1).

Example 2

Figure 3:
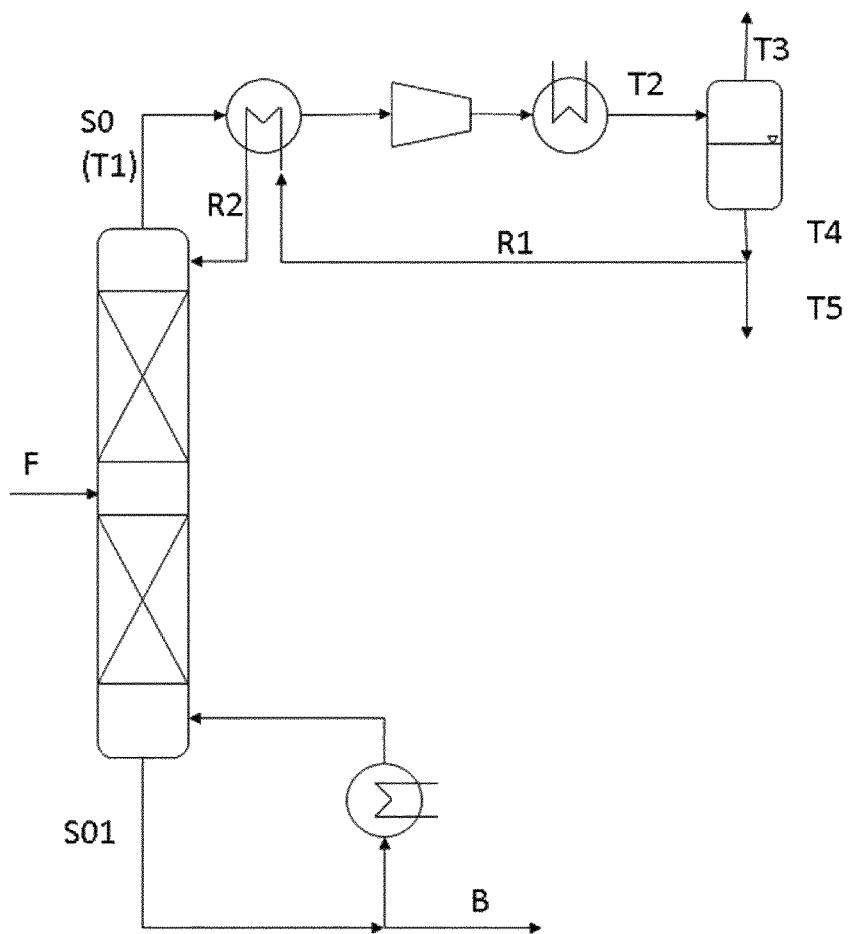

Example 2 was identical with example 1, except that the reflux stream R1, which represented the part of the stream T4 to be returned to the tower, was pre-cooled by heat-exchange with the stream T1 (S0) at the top of the tower to give a pre-cooled reflux stream R2, which formed the condensed portion of S0.
The setup is schematically shown in FIG. 3.

The temperature at the top of the tower remained the same as in example 1 (=temperature T1, S0), but the mass flow rate of stream T1 (S01) was now only 13.0 t/h. This stream was compressed to 16.7 bar and cooled to 35.1° C., whereas most of the stream condensed (stream T2). From the liquid stream T4, 8.7 t/h were taken and pre-cooled by heat-exchange with stream T1 (S0). After the heat exchange, the temperature of the pre-cooled reflux stream R2, which formed the condensed portion of S0, was −28.7° C. This stream was then returned to the top of the distillation tower, where it flashed.

The temperature at the bottom of the tower remained the same as in example 1 (=temperature of B, S0). Under these conditions the combined reboiler duty and electrical power for compression added up to 2.7 MW and was thus 16% lower than the energy required in the best comparative example (comp. example 1).

SHORT DESCRIPTION OF THE FIGURES

FIG. 1 shows a block diagram of the process according to Comparative Examples 1. In FIG. 1, the letters and numbers have the following meanings:
F, T1, T2, B streams according to a specifically preferred process as described in the examples
S0, S1a streams according to a preferred process as described in the general description and the examples
FIG. 2 shows a block diagram of the process according to Example 1. In FIG. 2, the letters and numbers have the following meanings:
F, T1, T2, T3, T4, T5, R, B streams according to a specifically preferred process as described in the examples
S0, S1a streams according to a preferred process as described in the general description and the examples
FIG. 3 shows a block diagram of the process for Example 2. In FIG. 3, the letters and numbers have the following meanings:
F, T1, T2, T3,
T4, T5, R1, R2, B streams according to a specifically preferred process as described in the examples
S0, S1a streams according to a preferred process as described in the general description and the examples

CITED LITERATURE

WO 2008/118265 A
WO 2004/037802 A

Ullmann's Encyclopedia of Industrial Chemistry, 5$^{th}$ edition, volume A 13 (1989) pages 443-466
EP 1 122 249 A1

The invention claimed is:
1. A process for preparing propylene oxide, the process comprising:
(i) providing a liquid feed stream comprising propene, hydrogen peroxide or a source of hydrogen peroxide, water, and an organic solvent;
(ii) passing the liquid feed stream into an epoxidation zone comprising an epoxidation catalyst comprising a titanium zeolite, and subjecting the liquid feed stream to epoxidation reaction conditions in the epoxidation zone, thereby obtaining a reaction mixture comprising propene, propylene oxide, water, and the organic solvent;
(iii) removing an effluent stream from the epoxidation zone, the effluent stream comprising propylene oxide, water, organic solvent, and propene; and
(iv) separating propene from the effluent stream by distillation, comprising
(iv.1) subjecting the effluent stream to distillation conditions in a distillation unit, thereby obtaining a gaseous top stream S0 enriched in propene compared to the effluent stream subjected to distillation conditions, and a liquid bottoms stream S01 enriched in propylene oxide, water and organic solvent compared to the effluent stream subjected to distillation conditions; and
(iv.2) returning a condensed portion of the gaseous top stream S0 to an upper part of the distillation unit.
2. The process of claim 1, wherein
the liquid feed stream further comprises propane;
the reaction mixture further comprises propane;
the effluent stream further comprises propane;
the separating is separating the propene and propane; and
the gaseous top stream S0 is enriched in the propene and propane.
3. The process of claim 1, wherein
the distillation unit employed is at least one distillation tower wherein the distillation tower has from 3 to 50 theoretical trays.
4. The process of claim 1, wherein
a rectifying section of the distillation unit consists of from 50 to 75% of theoretical trays and
a stripping section of the distillation unit consists of from 25 to 50% of theoretical trays.
5. The process of claim 1, wherein
the distillation unit is operated at a top pressure of from 0.5 to 2.8 bar.
6. The process of claim 1, wherein
the distillation unit is operated at a top temperature of from −70 to −30° C.
7. The process of claim 1, wherein
the gaseous top stream S0 removed from the distillation unit has a pressure of from 0.5 to 2.8 bar and a temperature of from −70 to −30° C.
8. The process of claim 1, wherein
the condensed portion of the gaseous top stream S0 is regulated so that an oxygen concentration in an uncondensed portion of the gaseous top stream S0 is less than 10 vol.-%.
9. The process of claim 1, further comprising:
condensing a portion of the gaseous top stream S0 by compression to a pressure of from 5 to 20 bar, and adjusting the temperature to be of from 20 to 50° C.

10. The process of claim 1, wherein of from 50 to 90 weight-% of the gaseous top stream S0, which form the condensed portion of the gaseous top stream S0, are returned to the upper part of the distillation unit.

11. The process of claim 1, wherein the condensed portion of the gaseous top stream S0 is returned to the upper part of the distillation unit at a top of the distillation unit or within a rectifying section of the distillation unit.

12. The process of claim 1, wherein the condensed portion of the gaseous top stream S0, which is returned to the upper part of the distillation unit in (iv.2), has a temperature of from 20 to 50° C.

13. The process of claim 1, wherein the condensed portion of the gaseous top stream S0 is heat exchanged with the gaseous top stream S0 prior to the returning to the upper part of the distillation unit.

14. The process of claim 1, wherein a temperature of the condensed portion of the gaseous top stream S0 is decreased after compression and prior to the returning to the upper part of the distillation unit by 35 to 80 K.

15. The process of claim 1, which is a continuation process.

* * * * *

UNITED STATES PATENT AND TRADEMARK OFFICE
CERTIFICATE OF CORRECTION

PATENT NO. : 10,435,381 B2
APPLICATION NO. : 16/318221
DATED : October 8, 2019
INVENTOR(S) : Joaquim Henrique Teles et al.

It is certified that error appears in the above-identified patent and that said Letters Patent is hereby corrected as shown below:

In the Specification

In Column 2, Line 6, delete "destillative" and insert -- distillative --, therefor.

In Column 10, Line 52, delete "a a" and insert -- a --, therefor.

In Column 15, Line 26, delete "10vol.-%" and insert -- 10 vol.-% --, therefor.

In Column 16, Line 18, delete "23" and insert -- 23, --, therefor.

In Column 16, Line 50, delete "JBW" and insert -- JBW, --, therefor.

In Column 17, Line 22, delete "Zr" and insert -- Zr, --, therefor.

In Column 17, Line 23, delete "Co,Ni," and insert -- Co, Ni, --, therefor.

In Column 17, Line 37, delete "27or 30to" and insert -- 27 or 30 to --, therefor.

In Column 17, Line 56, delete "SO1," and insert -- S01, --, therefor.

In Column 17, Line 59, delete "SO1." and insert -- S01. --, therefor.

In Column 18, Line 18, delete "Wherein" and insert -- wherein --, therefor.

In Column 18, Line 25, delete "90weight-%," and insert -- 90 weight-%, --, therefor.

In Column 18, Line 31, after "(i)," insert -- (ii), --, therefor.

In Column 20, Line 43, delete "a t" and insert -- at --, therefor.

Signed and Sealed this
Twenty-sixth Day of May, 2020

Andrei Iancu
*Director of the United States Patent and Trademark Office*

CERTIFICATE OF CORRECTION (continued)
U.S. Pat. No. 10,435,381 B2

In Column 22, Line 47, delete "mulitpoint" and insert -- multipoint --, therefor.

In Column 22, Line 58, delete "deioinized" and insert -- deionized --, therefor.

In Column 23, Line 32, delete "t" and insert -- to --, therefor.

In Column 28, Line 29, delete "02" and insert -- $O_2$ --, therefor.

In Column 29, Line 62, delete "examples" and insert -- examples. --, therefor.